(12) United States Patent
Kokish

(10) Patent No.: US 9,282,965 B2
(45) Date of Patent: Mar. 15, 2016

(54) APPARATUS AND METHODS FOR ENGAGING TISSUE

(75) Inventor: Arkady Kokish, Los Gatos, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 540 days.

(21) Appl. No.: 12/122,603

(22) Filed: May 16, 2008

(65) Prior Publication Data

US 2009/0287244 A1    Nov. 19, 2009

(51) Int. Cl.
*A61B 17/10*    (2006.01)
*A61B 17/08*    (2006.01)
*A61B 17/00*    (2006.01)

(52) U.S. Cl.
CPC ............. *A61B 17/10* (2013.01); *A61B 17/0057* (2013.01); *A61B 17/08* (2013.01); *A61B 17/083* (2013.01); *A61B 2017/00663* (2013.01)

(58) Field of Classification Search
CPC ............. A61B 17/128; A61B 17/1285; A61B 17/122; A61B 17/10; A61B 17/0487; A61B 17/08; A61B 17/22; A61B 2017/0488; A61B 17/081; A61B 17/083
USPC ......... 606/139, 142, 151, 157, 158, 213, 215, 606/216, 143, 75, 324; 24/132 WL, 132 R, 24/461, 464, 542, 543, 518, 528, 544, 559
See application file for complete search history.

(56) References Cited

U.S. PATENT DOCUMENTS

| 287,046 | A | 10/1883 | Norton |
|---|---|---|---|
| 438,400 | A | 10/1890 | Brennen |
| 556,082 | A | 3/1896 | Boeddinghaus |
| 1,088,393 | A | 2/1914 | Backus |
| 1,123,290 | A | 1/1915 | Von Herff |
| 1,242,139 | A | 10/1917 | Callahan |
| 1,331,401 | A | 2/1920 | Summers |

(Continued)

FOREIGN PATENT DOCUMENTS

| AU | 2003297432 | 7/2004 |
|---|---|---|
| CA | 2 339 060 | 2/2000 |

(Continued)

OTHER PUBLICATIONS

U.S. Appl. No. 12/897,358, filed Oct. 4, 2010, Carley.

(Continued)

*Primary Examiner* — Christopher L Templeton
(74) *Attorney, Agent, or Firm* — Workman Nydegger; Randy Shen

(57) ABSTRACT

An engaging element for engaging tissue is described. The engaging element may include a first member including at least one tissue engaging portion and a second member including at least one tissue engaging portion. The second member may be pivotally connected to the first member. The engaging element includes a locking mechanism operatively associated with the first and second member. The locking mechanism may be configured to inhibit the relative motion of the first and said second member. An engaging system for engaging tissue is described. The engaging system may include an engaging element for engaging tissue, a first member having at least one tissue engaging portion, and/or a second member including at least one tissue engaging portion. A method for engaging tissue is described. The method may include positioning an engaging element relative to an engaging element delivery device and/or to a portion of tissue.

19 Claims, 16 Drawing Sheets

(56) References Cited

U.S. PATENT DOCUMENTS

| | | |
|---|---|---|
| 1,480,935 A | 1/1924 | Gleason |
| 1,596,004 A | 8/1926 | De Bengoa |
| 1,647,958 A | 11/1927 | Ciarlante |
| 1,880,569 A | 10/1932 | Weis |
| 2,087,074 A | 7/1937 | Tucker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A * | 5/1970 | Blake .......................... 606/158 |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,682,180 A | 8/1972 | McFarlane |
| 3,757,629 A | 9/1973 | Schneider |
| 3,805,337 A | 4/1974 | Branstetter |
| 3,823,719 A * | 7/1974 | Cummings ................... 606/208 |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A * | 6/1976 | Murray ........................... 606/75 |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A * | 9/1978 | Williams ....................... 604/244 |
| 4,153,321 A * | 5/1979 | Pombrol ....................... 439/437 |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A * | 6/1981 | Kanamoto et al. ............ 606/142 |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A * | 5/1984 | Cerwin et al. ................ 606/158 |
| 4,475,544 A * | 10/1984 | Reis ............................ 606/86 R |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A * | 6/1985 | Kaplan et al. ................. 606/151 |
| 4,523,695 A | 6/1985 | Braun et al. |
| 4,525,157 A | 6/1985 | Valaincourt |
| 4,526,174 A | 7/1985 | Froehlich |
| 4,570,633 A * | 2/1986 | Golden ......................... 606/142 |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,651,737 A * | 3/1987 | Deniega ........................ 606/158 |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A * | 12/1990 | Blasnik et al. ................. 606/157 |
| 4,983,176 A * | 1/1991 | Cushman et al. ............. 606/151 |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,011,487 A * | 4/1991 | Shichman ..................... 606/158 |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,042,707 A | 8/1991 | Taheri |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |

(56) References Cited

U.S. PATENT DOCUMENTS

| | | |
|---|---|---|
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,259 A | 12/1992 | Inoue |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,209,756 A | 5/1993 | Seedhom et al. |
| 5,217,024 A | 6/1993 | Dorsey et al. |
| 5,222,971 A | 6/1993 | Willard et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A * | 9/1993 | Nash et al. .................. 606/142 |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A * | 4/1994 | Gourlay et al. ............. 606/142 |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,322,694 A | 6/1994 | Sixsmith |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| 5,383,897 A | 1/1995 | Wholey |
| RE34,866 E | 2/1995 | Kensey et al. |
| 5,392,978 A | 2/1995 | Velez et al. |
| 5,395,030 A | 3/1995 | Kuramoto et al. |
| 5,404,621 A | 4/1995 | Heinke |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A * | 11/1995 | Siska et al. .................... 606/151 |
| 5,464,416 A * | 11/1995 | Steckel ......................... 606/158 |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A * | 12/1995 | Zinreich et al. ............... 606/151 |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,484,420 A | 1/1996 | Russo |
| 5,486,195 A | 1/1996 | Myers et al. |
| 5,496,332 A | 3/1996 | Sierra et al. |
| 5,497,933 A | 3/1996 | DeFonzo et al. |
| 5,507,744 A | 4/1996 | Tay et al. |
| 5,507,755 A | 4/1996 | Gresl et al. |
| 5,510,115 A | 4/1996 | Breillatt, Jr. et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,626,614 A | 5/1997 | Hart |
| 5,634,936 A | 6/1997 | Linden et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,669,935 A | 9/1997 | Rosenman et al. |
| 5,674,231 A | 10/1997 | Green et al. |

(56) References Cited

U.S. PATENT DOCUMENTS

| | | | |
|---|---|---|---|
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,697,943 A | 12/1997 | Sauer et al. |
| 5,700,273 A | 12/1997 | Buelna et al. |
| 5,709,224 A | 1/1998 | Behl et al. |
| 5,713,899 A | 2/1998 | Marnay et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,736 A | 4/1998 | Volk |
| 5,735,873 A | 4/1998 | MacLean |
| 5,749,826 A | 5/1998 | Faulkner |
| 5,752,966 A | 5/1998 | Chang |
| 5,755,726 A | 5/1998 | Pratt et al. |
| 5,755,727 A | 5/1998 | Kontos |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A * | 7/1998 | Dolendo ............... 606/142 |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,217 A | 11/1998 | Ryan |
| 5,830,221 A | 11/1998 | Stein et al. |
| 5,833,698 A | 11/1998 | Hinchliffe et al. |
| 5,843,164 A | 12/1998 | Frantzen et al. |
| 5,843,167 A | 12/1998 | Dwyer et al. |
| 5,845,657 A | 12/1998 | Carberry et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,697 A | 5/1999 | Gifford, III et al. |
| 5,904,703 A | 5/1999 | Gilson |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A * | 7/1999 | Klein et al. ............... 606/60 |
| 5,928,251 A | 7/1999 | Aranyi et al. |
| 5,928,260 A | 7/1999 | Chin et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,972,023 A | 10/1999 | Tanner et al. |
| 5,976,161 A | 11/1999 | Kirsch et al. |
| 5,976,174 A | 11/1999 | Ruiz |
| 5,984,934 A * | 11/1999 | Ashby et al. ............ 606/151 |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,750 A | 2/2000 | Mastri |
| 6,024,756 A | 2/2000 | Huebsch et al. |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,074,395 A | 6/2000 | Trott et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,083,242 A | 7/2000 | Cook |
| 6,090,130 A | 7/2000 | Nash et al. |
| 6,095,155 A | 8/2000 | Criscuolo |
| 6,102,271 A | 8/2000 | Longo et al. |
| 6,110,184 A | 8/2000 | Weadock |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |

(56) References Cited

U.S. PATENT DOCUMENTS

| | | | |
|---|---|---|---|
| 6,117,159 A | 9/2000 | Huebsch et al. | |
| 6,120,513 A | 9/2000 | Bailey et al. | |
| 6,120,524 A | 9/2000 | Taheri | |
| 6,126,675 A | 10/2000 | Schervinsky et al. | |
| 6,136,010 A | 10/2000 | Modesitt et al. | |
| 6,146,385 A | 11/2000 | Torrie et al. | |
| 6,149,660 A | 11/2000 | Laufer et al. | |
| 6,149,667 A | 11/2000 | Hovland et al. | |
| 6,152,144 A | 11/2000 | Lesh et al. | |
| 6,152,936 A | 11/2000 | Christy et al. | |
| 6,152,937 A | 11/2000 | Peterson et al. | |
| 6,161,263 A | 12/2000 | Anderson | |
| 6,165,204 A | 12/2000 | Levinson et al. | |
| 6,171,277 B1 | 1/2001 | Ponzi | |
| 6,171,329 B1 | 1/2001 | Shaw et al. | |
| 6,174,322 B1 | 1/2001 | Schneidt | |
| 6,179,849 B1 | 1/2001 | Yencho et al. | |
| 6,179,860 B1 | 1/2001 | Fulton, III et al. | |
| 6,183,775 B1 | 2/2001 | Ventouras | |
| 6,193,708 B1 | 2/2001 | Ken et al. | |
| 6,193,734 B1 | 2/2001 | Bolduc et al. | |
| 6,197,042 B1 | 3/2001 | Ginn et al. | |
| 6,198,974 B1 | 3/2001 | Webster, Jr. | |
| 6,200,329 B1 | 3/2001 | Fung et al. | |
| 6,200,330 B1 | 3/2001 | Benderev et al. | |
| 6,206,895 B1 | 3/2001 | Levinson | |
| 6,206,913 B1 | 3/2001 | Yencho et al. | |
| 6,206,931 B1 | 3/2001 | Cook et al. | |
| 6,210,407 B1 | 4/2001 | Webster | |
| 6,210,418 B1 * | 4/2001 | Storz et al. | 606/142 |
| 6,220,248 B1 | 4/2001 | Voegele et al. | |
| 6,221,102 B1 | 4/2001 | Baker et al. | |
| 6,231,561 B1 | 5/2001 | Frazier et al. | |
| 6,238,705 B1 | 5/2001 | Liu et al. | |
| 6,241,740 B1 | 6/2001 | Davis et al. | |
| 6,245,079 B1 | 6/2001 | Nobles et al. | |
| 6,248,124 B1 | 6/2001 | Pedros et al. | |
| 6,254,617 B1 | 7/2001 | Spence et al. | |
| 6,254,642 B1 | 7/2001 | Taylor | |
| 6,258,115 B1 | 7/2001 | Dubrul | |
| 6,267,773 B1 * | 7/2001 | Gadberry et al. | 606/151 |
| 6,273,903 B1 * | 8/2001 | Wilk | 606/219 |
| 6,276,704 B1 | 8/2001 | Suiter | |
| 6,277,140 B2 | 8/2001 | Ginn et al. | |
| 6,280,460 B1 | 8/2001 | Bolduc et al. | |
| 6,287,322 B1 | 9/2001 | Zhu et al. | |
| 6,287,335 B1 | 9/2001 | Drasler et al. | |
| 6,290,674 B1 | 9/2001 | Roue et al. | |
| 6,296,657 B1 | 10/2001 | Brucker | |
| 6,302,870 B1 | 10/2001 | Jacobsen et al. | |
| 6,302,898 B1 | 10/2001 | Edwards et al. | |
| 6,305,891 B1 | 10/2001 | Burlingame | |
| 6,309,416 B1 | 10/2001 | Swanson et al. | |
| 6,319,258 B1 | 11/2001 | McAllen, III et al. | |
| 6,322,580 B1 | 11/2001 | Kanner | |
| 6,328,727 B1 | 12/2001 | Frazier et al. | |
| 6,329,386 B1 | 12/2001 | Mollison | |
| 6,334,865 B1 | 1/2002 | Redmond et al. | |
| 6,348,064 B1 | 2/2002 | Kanner | |
| 6,355,052 B1 | 3/2002 | Neuss et al. | |
| 6,358,258 B1 | 3/2002 | Arcia et al. | |
| 6,375,671 B1 | 4/2002 | Kobayashi et al. | |
| D457,958 S | 5/2002 | Dycus | |
| 6,383,208 B1 | 5/2002 | Sancoff et al. | |
| 6,391,048 B1 | 5/2002 | Ginn et al. | |
| 6,395,015 B1 | 5/2002 | Borst et al. | |
| 6,398,752 B1 | 6/2002 | Sweezer et al. | |
| 6,402,765 B1 | 6/2002 | Monassevitch et al. | |
| 6,409,739 B1 | 6/2002 | Nobles et al. | |
| 6,419,669 B1 | 7/2002 | Frazier et al. | |
| 6,421,899 B1 | 7/2002 | Zitnay | |
| 6,423,054 B1 | 7/2002 | Ouchi | |
| 6,425,911 B1 | 7/2002 | Akerfeldt et al. | |
| 6,428,472 B1 | 8/2002 | Haas | |
| 6,428,548 B1 | 8/2002 | Durgin et al. | |
| 6,443,158 B1 | 9/2002 | Lafontaine et al. | |
| 6,443,963 B1 | 9/2002 | Baldwin et al. | |
| 6,447,540 B1 | 9/2002 | Fontaine et al. | |
| 6,450,391 B1 | 9/2002 | Kayan et al. | |
| 6,455,053 B1 | 9/2002 | Okada et al. | |
| 6,458,130 B1 | 10/2002 | Frazier et al. | |
| 6,461,364 B1 | 10/2002 | Ginn et al. | |
| 6,482,224 B1 | 11/2002 | Michler et al. | |
| 6,488,692 B1 | 12/2002 | Spence et al. | |
| 6,500,115 B2 | 12/2002 | Krattiger et al. | |
| 6,506,210 B1 | 1/2003 | Kanner | |
| 6,508,828 B1 | 1/2003 | Akerfeldt et al. | |
| 6,514,280 B1 | 2/2003 | Gilson | |
| 6,517,555 B1 | 2/2003 | Caro | |
| 6,517,569 B2 | 2/2003 | Mikus et al. | |
| 6,527,737 B2 | 3/2003 | Kaneshige | |
| 6,533,762 B2 | 3/2003 | Kanner et al. | |
| 6,533,812 B2 | 3/2003 | Swanson et al. | |
| 6,537,288 B2 | 3/2003 | Vargas et al. | |
| 6,544,230 B1 | 4/2003 | Flaherty et al. | |
| 6,547,806 B1 | 4/2003 | Ding | |
| 6,551,319 B2 | 4/2003 | Lieberman | |
| 6,558,349 B1 | 5/2003 | Kirkman | |
| 6,569,173 B1 | 5/2003 | Blatter et al. | |
| 6,569,185 B2 | 5/2003 | Ungs | |
| 6,572,629 B2 | 6/2003 | Kalloo et al. | |
| 6,578,585 B1 | 6/2003 | Stachowski et al. | |
| 6,582,452 B2 | 6/2003 | Coleman et al. | |
| 6,582,482 B2 | 6/2003 | Gillman et al. | |
| 6,596,012 B2 | 7/2003 | Akerfeldt et al. | |
| 6,596,013 B2 | 7/2003 | Yang et al. | |
| 6,599,303 B1 | 7/2003 | Peterson et al. | |
| 6,599,311 B1 | 7/2003 | Biggs et al. | |
| 6,602,263 B1 | 8/2003 | Swanson et al. | |
| 6,610,072 B1 | 8/2003 | Christy et al. | |
| 6,613,059 B2 | 9/2003 | Schaller et al. | |
| 6,613,060 B2 | 9/2003 | Adams et al. | |
| 6,616,686 B2 | 9/2003 | Coleman et al. | |
| 6,620,165 B2 | 9/2003 | Wellisz | |
| 6,623,509 B2 | 9/2003 | Ginn | |
| 6,623,510 B2 | 9/2003 | Carley et al. | |
| 6,626,918 B1 | 9/2003 | Ginn et al. | |
| 6,626,919 B1 | 9/2003 | Swanstrom | |
| 6,626,920 B2 | 9/2003 | Whayne | |
| 6,626,930 B1 | 9/2003 | Allen et al. | |
| 6,632,197 B2 | 10/2003 | Lyon | |
| 6,632,238 B2 | 10/2003 | Ginn et al. | |
| 6,634,537 B2 | 10/2003 | Chen | |
| 6,645,205 B2 | 11/2003 | Ginn | |
| 6,645,225 B1 | 11/2003 | Atkinson | |
| 6,645,255 B2 | 11/2003 | Sanduja et al. | |
| 6,652,538 B2 | 11/2003 | Kayan et al. | |
| 6,652,556 B1 | 11/2003 | VanTassel et al. | |
| 6,663,633 B1 | 12/2003 | Pierson, III | |
| 6,663,655 B2 | 12/2003 | Ginn et al. | |
| 6,669,714 B2 | 12/2003 | Coleman et al. | |
| 6,673,083 B1 * | 1/2004 | Kayan et al. | 606/143 |
| 6,676,665 B2 | 1/2004 | Foley et al. | |
| 6,676,671 B2 | 1/2004 | Robertson et al. | |
| 6,676,685 B2 | 1/2004 | Pedros et al. | |
| 6,679,904 B2 | 1/2004 | Gleeson et al. | |
| 6,685,707 B2 | 2/2004 | Roman et al. | |
| 6,689,147 B1 | 2/2004 | Koster, Jr. | |
| 6,695,867 B2 | 2/2004 | Ginn et al. | |
| 6,699,256 B1 | 3/2004 | Logan et al. | |
| 6,702,826 B2 | 3/2004 | Liddicoat et al. | |
| 6,712,836 B1 | 3/2004 | Berg et al. | |
| 6,712,837 B2 | 3/2004 | Akerfeldt et al. | |
| 6,719,777 B2 | 4/2004 | Ginn et al. | |
| 6,726,704 B1 | 4/2004 | Loshakove et al. | |
| 6,736,822 B2 | 5/2004 | McClellan et al. | |
| 6,743,195 B2 | 6/2004 | Zucker | |
| 6,743,243 B1 | 6/2004 | Roy et al. | |
| 6,743,259 B2 | 6/2004 | Ginn | |
| 6,746,472 B2 | 6/2004 | Frazier et al. | |
| 6,749,621 B2 | 6/2004 | Pantages et al. | |
| 6,749,622 B2 | 6/2004 | McGuckin et al. | |
| 6,752,813 B2 | 6/2004 | Goldfarb et al. | |
| 6,755,842 B2 | 6/2004 | Kanner et al. | |

(56) References Cited

U.S. PATENT DOCUMENTS

| | | | |
|---|---|---|---|
| 6,758,855 B2 | 7/2004 | Fulton, III et al. |
| 6,767,356 B2 | 7/2004 | Kanner et al. |
| 6,776,784 B2 | 8/2004 | Ginn |
| 6,776,785 B1 | 8/2004 | Yencho et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,391 B1 | 11/2005 | Gazzani |
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,220,268 B2 | 5/2007 | Blatter |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 * | 1/2008 | Buckman et al. ............ 606/157 |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,678,135 B2 | 3/2010 | Maahs et al. |
| 7,780,696 B2 | 8/2010 | Daniel et al. |
| 7,799,042 B2 | 9/2010 | Williamson, IV et al. |
| 7,806,904 B2 | 10/2010 | Carley et al. |
| 7,819,895 B2 | 10/2010 | Ginn et al. |
| 7,841,502 B2 | 11/2010 | Walberg et al. |
| 7,842,068 B2 | 11/2010 | Ginn |
| 7,850,709 B2 | 12/2010 | Cummins et al. |
| 7,850,797 B2 | 12/2010 | Carley et al. |
| 7,854,810 B2 | 12/2010 | Carley et al. |
| 7,857,828 B2 | 12/2010 | Jabba et al. |
| 7,875,054 B2 | 1/2011 | LaFontaine |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelov |
| 8,172,749 B2 | 5/2012 | Melsheimer |
| 8,226,666 B2 | 7/2012 | Zarbatany et al. |
| 8,409,228 B2 | 4/2013 | Blatter et al. |
| 2001/0007077 A1 | 7/2001 | Ginn et al. |
| 2001/0021855 A1 | 9/2001 | Levinson |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0058960 A1 | 5/2002 | Hudson et al. |
| 2002/0062104 A1 | 5/2002 | Ashby et al. |
| 2002/0077657 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0151963 A1 | 10/2002 | Brown et al. |
| 2002/0169475 A1 | 11/2002 | Gainor et al. |
| 2002/0183786 A1 | 12/2002 | Girton |
| 2002/0183787 A1 | 12/2002 | Wahr et al. |
| 2002/0198562 A1 | 12/2002 | Ackerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2003/0208211 A1 | 11/2003 | Kortenbach |
| 2004/0009205 A1 | 1/2004 | Sawhney |
| 2004/0009289 A1 | 1/2004 | Carley et al. |
| 2004/0010285 A1 | 1/2004 | Carley et al. |

(56) References Cited

U.S. PATENT DOCUMENTS

| | | |
|---|---|---|
| 2004/0039414 A1 | 2/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chandusko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0245876 A1 | 11/2005 | Khosravi et al. |
| 2005/0256532 A1 | 11/2005 | Nayak et al. |
| 2005/0267524 A1 | 12/2005 | Chanduszko |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0100664 A1 | 5/2006 | Pai et al. |
| 2006/0142784 A1 | 6/2006 | Kontos |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0195125 A1* | 8/2006 | Sakakine et al. ............... 606/157 |
| 2006/0206146 A1 | 9/2006 | Tenerz |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0287674 A1 | 12/2006 | Ginn et al. |
| 2006/0293698 A1* | 12/2006 | Douk ............................ 606/142 |
| 2007/0005093 A1 | 1/2007 | Cox |
| 2007/0010851 A1 | 1/2007 | Chanduszko et al. |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027476 A1* | 2/2007 | Harris et al. ................... 606/232 |
| 2007/0027525 A1 | 2/2007 | Ben-Muvhar |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0073337 A1 | 3/2007 | Abbott et al. |
| 2007/0078302 A1 | 4/2007 | Ortiz et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1* | 5/2007 | Hilal et al. ..................... 606/157 |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0149996 A1 | 6/2007 | Coughlin |
| 2007/0172430 A1 | 7/2007 | Brito et al. |
| 2007/0179527 A1 | 8/2007 | Eskuri et al. |
| 2007/0185529 A1 | 8/2007 | Coleman et al. |
| 2007/0185530 A1 | 8/2007 | Chin-Chen et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1 | 1/2008 | Walberg et al. |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0097509 A1 | 4/2008 | Beyar et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0208225 A1 | 8/2008 | Seibold et al. |
| 2008/0210737 A1 | 9/2008 | Ginn et al. |
| 2008/0221616 A1 | 9/2008 | Ginn et al. |
| 2008/0243148 A1* | 10/2008 | Mikkaichi et al. ............ 606/144 |
| 2008/0243182 A1 | 10/2008 | Bates et al. |
| 2008/0249504 A1 | 10/2008 | Lattouf et al. |
| 2008/0269801 A1 | 10/2008 | Coleman et al. |
| 2008/0269802 A1 | 10/2008 | Coleman et al. |

(56) References Cited

U.S. PATENT DOCUMENTS

| | | | |
|---|---|---|---|
| 2008/0272173 | A1 | 11/2008 | Coleman et al. |
| 2008/0287988 | A1 | 11/2008 | Smith et al. |
| 2008/0294001 | A1 | 11/2008 | Surti |
| 2008/0300628 | A1 | 12/2008 | Ellingwood |
| 2008/0312666 | A1 | 12/2008 | Ellingwood et al. |
| 2008/0312667 | A1 | 12/2008 | Drasler et al. |
| 2008/0312686 | A1 | 12/2008 | Ellingwood |
| 2008/0312740 | A1 | 12/2008 | Wachter et al. |
| 2008/0319475 | A1 | 12/2008 | Clark |
| 2009/0054912 | A1 | 2/2009 | Heanue et al. |
| 2009/0105728 | A1 | 4/2009 | Noda et al. |
| 2009/0112306 | A1 | 4/2009 | Bonsignore et al. |
| 2009/0132031 | A1 | 5/2009 | Cook et al. |
| 2009/0137900 | A1 | 5/2009 | Bonner et al. |
| 2009/0157101 | A1 | 6/2009 | Reyes et al. |
| 2009/0157102 | A1 | 6/2009 | Reynolds et al. |
| 2009/0171388 | A1 | 7/2009 | Dave et al. |
| 2009/0177212 | A1 | 7/2009 | Carley et al. |
| 2009/0187215 | A1 | 7/2009 | Mackiewicz et al. |
| 2009/0216267 | A1 | 8/2009 | Willard et al. |
| 2009/0221960 | A1 | 9/2009 | Albrecht et al. |
| 2009/0227938 | A1 | 9/2009 | Fasching et al. |
| 2009/0230168 | A1 | 9/2009 | Coleman et al. |
| 2009/0254119 | A1 | 10/2009 | Sibbitt, Jr. et al. |
| 2009/0312789 | A1 | 12/2009 | Kassab et al. |
| 2010/0042144 | A1 | 2/2010 | Bennett |
| 2010/0114156 | A1 | 5/2010 | Mehl |
| 2010/0114159 | A1 | 5/2010 | Roorda et al. |
| 2010/0130965 | A1 | 5/2010 | Sibbitt, Jr. et al. |
| 2010/0168790 | A1 | 7/2010 | Clark |
| 2010/0179567 | A1 | 7/2010 | Voss et al. |
| 2010/0179571 | A1 | 7/2010 | Voss |
| 2010/0179572 | A1 | 7/2010 | Voss et al. |
| 2010/0179589 | A1 | 7/2010 | Roorda et al. |
| 2010/0179590 | A1 | 7/2010 | Fortson et al. |
| 2010/0185234 | A1 | 7/2010 | Fortson et al. |
| 2010/0217132 | A1 | 8/2010 | Ellingwood et al. |
| 2010/0249828 | A1 | 9/2010 | Mavani et al. |
| 2011/0066163 | A1 | 3/2011 | Cho et al. |
| 2011/0082495 | A1 | 4/2011 | Ruiz |
| 2011/0178548 | A1 | 7/2011 | Tenerz |
| 2011/0270282 | A1 | 11/2011 | Lemke |
| 2012/0035630 | A1 | 2/2012 | Roorda |
| 2012/0101520 | A1 | 4/2012 | Ginn et al. |
| 2012/0245603 | A1 | 9/2012 | Voss |
| 2012/0245623 | A1 | 9/2012 | Kariniemi et al. |
| 2012/0245626 | A1 | 9/2012 | Ellingwood et al. |
| 2012/0310261 | A1 | 12/2012 | Cummins et al. |
| 2013/0006274 | A1 | 1/2013 | Walberg et al. |
| 2013/0338708 | A1 | 12/2013 | Cummins et al. |
| 2014/0142624 | A1 | 5/2014 | Pantages et al. |
| 2014/0309686 | A1 | 10/2014 | Ginn et al. |
| 2014/0364903 | A1 | 12/2014 | Roorda et al. |
| 2015/0073471 | A1 | 3/2015 | Clark |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |

(56) References Cited

FOREIGN PATENT DOCUMENTS

| WO | WO 2004/004578 | 1/2004 |
|----|----------------|--------|
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/945,646, filed Nov. 12, 2010, Carley et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 10/435,104, Jan. 12, 2011, Issue Notification.
U.S. Appl. No. 10/638,115, Dec. 22, 2010, Issue Notification.
U.S. Appl. No. 11/113,549, Jan. 4, 2011, Office Action.
U.S. Appl. No. 12/113,851, Dec. 16, 2010, Office Action.
U.S. Appl. No. 12/114,091, Dec. 17, 2010, Office Action.
U.S. Appl. No. 12/402,398, Jan. 24, 2011, Office Action.
U.S. Appl. No. 12/945,646, Jan. 20, 2011, Office Action.
U.S. Appl. No. 13/017,636, filed Jan. 31, 2011, Carley et al.
U.S. Appl. No. 10/616,832, Jan. 26, 2011, Issue Notification.
U.S. Appl. No. 11/152,562, Jan. 26, 2011, Issue Notification.
U.S. Appl. No. 13/026,989, filed Feb. 14, 2011, Cummins.
U.S. Appl. No. 10/264,306, Feb. 16, 2011, Issue Notification.
U.S. Appl. No. 11/767,818, Feb. 16, 2011, Office Action.
U.S. Appl. No. 13/030,922, filed Feb. 18, 2011, Cummins.
U.S. Appl. No. 10/356,214, Feb. 23, 2011, Issue Notification.
U.S. Appl. No. 13/039,087, filed Mar. 2, 2011, Palermo et al.
U.S. Appl. No. 11/852,190, Mar. 2, 2011, Office Action.
U.S. Appl. No. 11/958,281, Mar. 10, 2011, Office Action.
U.S. Appl. No. 11/532,576, Mar. 16, 2011, Issue Notification.
U.S. Appl. No. 11/396,731, Mar. 22, 2011, Office Action.
U.S. Appl. No. 11/427,297, Mar. 21, 2011, Office Action.
U.S. Appl. No. 10/682,459, Apr. 1, 2011, Notice of Allowance.
U.S. Appl. No. 12/403,277, Mar. 31, 2011, Office Action.
U.S. Appl. No. 10/147,774, Apr. 6, 2011, Issue Notification.
U.S. Appl. No. 60/693,531, filed Jun. 24, 2005, Carly.
U.S. Appl. No. 60/696,069, filed Jul. 1, 2005, Pantages et al.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/097,072, filed Sep. 15, 2008, Sibbitt Jr. et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 12/481,377, filed Jun. 9, 2009, Clark.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 12/961,331, filed Dec. 6, 2010, Voss.
U.S. Appl. No. 12/966,923, filed Dec. 13, 2010, Cummins et al.
"Hand tool for forming telephone connections—comprises pliers with reciprocably driven ram crimping clip around conductors against anvil", Derwent-ACC-No. 1978-B8090A.
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
U.S. Appl. No. 12/143,020, Aug. 31, 2011, Office Action.
U.S. Appl. No. 12/897,358, Aug. 22, 2011, Office Action.

(56) References Cited

OTHER PUBLICATIONS

Marshall A.C., Lock J.E., Structural and Compliant Anatomy of the Patent Foramen Ovale in Patients Undergoing Transcatheter Closure, Am Heart J Aug. 2000; 140(2); pp. 303-307.

MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.

Michael Gianturco, A Play on Catheterization, Forbes, Dec. 1996, p. 146, vol. 158—No. 15.

OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.

P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive. org, Jun. 1998, Original Publisher: http://prostar.com, may also be found at http://web.archive.org/web/19980630040429/www. perclose.com/html/prstrxl.html.

SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Stretch Comb by Scunci, retrieved via internet at www.scunci.com/ productdetail by examiner on Oct. 9, 2007, publication date unavailable.

Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

Sy Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Taber's Cyclopedic Medical Dictionary, 18th Ed. 1997, pp. 747 and 1420.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.

Ut Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 09/478,179, Nov. 6, 2000, Notice of Allowance.
U.S. Appl. No. 09/546,998, May 6, 2002, Notice of Allowance.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/933,299, Feb. 26, 2003, Office Action.
U.S. Appl. No. 09/933,299, Jun. 16, 2003, Notice of Allowance.
U.S. Appl. No. 09/948,813, Jan. 31, 2003, Notice of Allowance.
U.S. Appl. No. 09/949,398, Mar. 4, 2003, Office Action.
U.S. Appl. No. 09/949,398, Jul. 28, 2003, Notice of Allowance.
U.S. Appl. No. 09/949,438, Dec. 17, 2002, Office Action.
U.S. Appl. No. 09/949,438, Apr. 21, 2003, Notice of Allowance.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/006,400, Jan. 2, 2009, Office Action.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/006,400, Apr. 27, 2010, Notice of Allowance.
U.S. Appl. No. 10/006,400, Aug. 2, 2010, Notice of Allowance.
U.S. Appl. No. 10/081,717, Sep. 29, 2003, Notice of Allowance.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,726, Apr. 11, 2003, Notice of Allowance.
U.S. Appl. No. 10/081,726, Jun. 9, 2003, Notice of Allowance.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/147,774, Mar. 18, 2009, Office Action.
U.S. Appl. No. 10/147,774, Oct. 26, 2009, Office Action.

(56) References Cited

OTHER PUBLICATIONS

U.S. Appl. No. 10/147,774, Jun. 8, 2010, Office Action.
U.S. Appl. No. 10/147,774, Dec. 2, 2010, Notice of Allowance.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Response to Rule 312 Communication.
U.S. Appl. No. 10/264,306, Feb. 9, 2005, Office Action.
U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/264,306, Feb. 26, 2009, Office Action.
U.S. Appl. No. 10/264,306, Aug. 13, 2009, Office Action.
U.S. Appl. No. 10/264,306, Jan. 27, 2010, Office Action.
U.S. Appl. No. 10/264,306, Jun. 15, 2010, Office Action.
U.S. Appl. No. 10/264,306, Oct. 29, 2010, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/356,214, Apr. 29, 2009, Office Action.
U.S. Appl. No. 10/356,214, Jan. 13, 2010, Notice of Allowance.
U.S. Appl. No. 10/356,214, May 13, 2010, Notice of Allowance.
U.S. Appl. No. 10/356,214, Sep. 3, 2010, Notice of Allowance.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Examiner's Amendment.
U.S. Appl. No. 10/435,104, May 16, 2006, Office Action.
U.S. Appl. No. 10/435,104, Dec. 28, 2006, Notice of Allowance.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/435,104, Dec. 22, 2008, Notice of Allowance.
U.S. Appl. No. 10/435,104, Jul. 23, 2009, Notice of Allowance.
U.S. Appl. No. 10/435,104, Jan. 20, 2010, Notice of Allowance.
U.S. Appl. No. 10/435,104, Jun. 2, 2010, Office Action.
U.S. Appl. No. 10/435,104, Oct. 5, 2010, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/517,004, Feb. 10, 2009, Notice of Allowance.
U.S. Appl. No. 10/517,004, Mar. 24, 2009, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/517,004, Apr. 23, 2010, Notice of Allowance.
U.S. Appl. No. 10/517,004, Aug. 3, 2010, Notice of Allowance.
U.S. Appl. No. 10/517,004, Nov. 23, 2010, Issue Notification.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/541,083, Sep. 30, 2009, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/541,083, Aug. 17, 2010, Notice of Allowance.
U.S. Appl. No. 10/541,083, Dec. 1, 2010, Issue Notification.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/616,832, Jul. 21, 2009, Office Action.
U.S. Appl. No. 10/616,832, Jan. 11, 2010, Notice of Allowance.
U.S. Appl. No. 10/616,832, May 12, 2010, Notice of Allowance.
U.S. Appl. No. 10/616,832, Sep. 20, 2010, Notice of Allowance.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/638,115, May 7, 2009, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/638,115, Aug. 13, 2010, Notice of Allowance.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/667,144, Mar. 24, 2009, Office Action.
U.S. Appl. No. 10/667,144, Nov. 23, 2009, Office Action.
U.S. Appl. No. 10/667,144, Jun. 22, 2010, Office Action.
U.S. Appl. No. 10/669,313, Oct. 31, 2005, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/682,459, Dec. 4, 2008, Office Action.
U.S. Appl. No. 10/682,459, Jun. 10, 2009, Office Action.
U.S. Appl. No. 10/682,459, Dec. 23, 2009, Office Action.
U.S. Appl. No. 10/682,459, Apr. 28, 2010, Office Action.
U.S. Appl. No. 10/682,459, Oct. 12, 2010, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/787,073, Aug. 13, 2009, Office Action.
U.S. Appl. No. 10/787,073, Feb. 17, 2010, Notice of Allowance.
U.S. Appl. No. 10/787,073, Aug. 25, 2010, Notice of Allowance.
U.S. Appl. No. 10/787,073, Sep. 15, 2010, Issue Notification.
U.S. Appl. No. 10/908,721, Oct. 19, 2006, Office Action.
U.S. Appl. No.,10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 10/908,721, Jun. 23, 2009, Office Action.
U.S. Appl. No. 10/908,721, Feb. 2, 2010, Office Action.
U.S. Appl. No. 11/048,503, Mar. 13, 2009, Office Action.
U.S. Appl. No. 11/048,503, Jun. 26, 2009, Office Action.
U.S. Appl. No. 11/048,503, Jan. 11, 2010, Notice of Allowance.

(56) References Cited

OTHER PUBLICATIONS

U.S. Appl. No. 11/048,503, Apr. 26, 2010, Notice of Allowance.
U.S. Appl. No. 11/048,503, Jul. 30, 2010, Notice of Allowance.
U.S. Appl. No. 11/048,503, Dec. 8, 2010, Issue Notification.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/113,549, Jul. 21, 2009, Office Action.
U.S. Appl. No. 11/113,549, Jul. 6, 2010, Office Action.
U.S. Appl. No. 11/152,562, May 13, 2008, Office Action.
U.S. Appl. No. 11/152,562, Feb. 13, 2009, Office Action.
U.S. Appl. No. 11/152,562, Jul. 6, 2009, Office Action.
U.S. Appl. No. 11/152,562, Mar. 31, 2010, Office Action.
U.S. Appl. No. 11/152,562, Sep. 16, 2010, Notice of Allowance.
U.S. Appl. No. 11/198,811, Aug. 26, 2008, Office Action.
U.S. Appl. No. 11/198,811, Apr. 6, 2009, Office Action.
U.S. Appl. No. 11/198,811, Sep. 22, 2009, Office Action.
U.S. Appl. No. 11/198,811, Jun. 29, 2010, Notice of Allowance.
U.S. Appl. No.,11/198,811, Oct. 20, 2010, Issue Notification.
U.S. Appl. No. 11/344,793, Jan. 22, 2009, Office Action.
U.S. Appl. No. 11/344,868, Mar. 25, 2009, Office Action.
U.S. Appl. No. 11/344,891, Apr. 29, 2008, Office Action.
U.S. Appl. No. 11/344,891, Dec. 8, 2008, Office Action.
U.S. Appl. No. 11/344,891, Feb. 26, 2009, Office Action.
U.S. Appl. No. 11/344,891, Oct. 7, 2009, Office Action.
U.S. Appl. No. 11/344,891, May 7, 2010, Office Action.
U.S. Appl. No. 11/390,586, Jun. 24, 2009, Office Action.
U.S. Appl. No. 11/390,586, Jul. 6, 2010, Office Action.
U.S. Appl. No. 11/396,141, May 22, 2009, Office Action.
U.S. Appl. No. 11/396,141, Aug. 26, 2009, Office Action.
U.S. Appl. No. 11/396,141, May 4, 2010, Office Action.
U.S. Appl. No. 11/396,731, Feb. 13, 2009, Office Action.
U.S. Appl. No. 11/396,731, May 22, 2009, Office Action.
U.S. Appl. No. 11/396,731, Jun. 29, 2010, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/406,203, Mar. 3, 2009, Office Action.
U.S. Appl. No. 11/406,203, Sep. 16, 2009, Office Action.
U.S. Appl. No. 11/406,203, Jun. 18, 2010, Notice of Allowance.
U.S. Appl. No. 11/406,203, Oct. 6, 2010, Issue Notification.
U.S. Appl. No. 11/411,925, Jun. 6, 2007, Office Action.
U.S. Appl. No. 11/411,925, Feb. 5, 2008, Office Action.
U.S. Appl. No. 11/411,925, Jan. 12, 2009, Office Action.
U.S. Appl. No. 11/411,925, Sep. 10, 2009, Office Action.
U.S. Appl. No. 11/427,297, Jan. 30, 2009, Office Action.
U.S. Appl. No. 11/427,297, Sep. 15, 2009, Office Action.
U.S. Appl. No. 11/427,297, Sep. 15, 2010, Office Action.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/427,309, Nov. 15, 2010, Office Action.
U.S. Appl. No. 11/455,993, Feb. 17, 2009, Office Action.
U.S. Appl. No. 11/455,993, Dec. 16, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 11/532,325, Jan. 5, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/532,576, Oct. 13, 2010, Notice of Allowance.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/675,462, Dec. 10, 2009, Office Action.
U.S. Appl. No. 11/675,462, Aug. 31, 2010, Office Action.
U.S. Appl. No. 11/744,089, Nov. 26, 2008, Office Action.
U.S. Appl. No. 11/744,089, Aug. 14, 2009, Office Action.
U.S. Appl. No. 11/757,108, Nov. 25, 2009, Office Action.
U.S. Appl. No. 11/767,818, Dec. 24, 2009, Office Action.
U.S. Appl. No. 11/767,818, Mar. 22, 2010, Office Action.
U.S. Appl. No. 11/767,818, Sep. 30, 2010, Office Action.
U.S. Appl. No. 11/852,190, Jun. 24, 2010, Office Action.
U.S. Appl. No. 11/852,190, Nov. 1, 2010, Office Action.
U.S. Appl. No. 11/958,281, Sep. 2, 2010, Office Action.
U.S. Appl. No. 11/958,281, Oct. 8, 2010, Office Action.
U.S. Appl. No. 11/958,295, Aug. 27, 2009, Office Action.
U.S. Appl. No. 11/958,295, May 25, 2010, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 11/959,334, Apr. 14, 2010, Notice of Allowance.
U.S. Appl. No. 11/959,334, Jul. 23, 2010, Notice of Allowance.
U.S. Appl. No. 11/959,334, Nov. 10, 2010, Issue Notification.
U.S. Appl. No. 12/106,928, Jan. 23, 2009, Office Action.
U.S. Appl. No. 12/106,928, Oct. 5, 2009, Office Action.
U.S. Appl. No. 12/106,928, May 10, 2010, Office Action.
U.S. Appl. No. 12/106,928, Oct. 25, 2010, Office Action.
U.S. Appl. No. 12/106,937, Mar. 30, 2009, Office Action.
U.S. Appl. No. 12/106,937, Nov. 18, 2009, Office Action.
U.S. Appl. No. 12/113,851, Apr. 27, 2010, Office Action.
U.S. Appl. No. 12/113,851, Jun. 24, 2010, Office Action.
U.S. Appl. No. 12/114,031, Oct. 5, 2010, Office Action.
U.S. Appl. No. 12/114,031, Nov. 22, 2010, Office Action.
U.S. Appl. No. 12/402,398, Mar. 9, 2010, Office Action.
U.S. Appl. No. 12/402,398, May 20, 2010, Office Action.
U.S. Appl. No. 12/403,256, Dec. 16, 2009, Office Action.
U.S. Appl. No. 12/403,256, Mar. 30, 2010, Office Action.
U.S. Appl. No. 12/403,256, Aug. 19, 2010, Notice of Allowance.
U.S. Appl. No. 12/403,256, Nov. 23, 2010, Issue Notification.
U.S. Appl. No. 12/403,277, Jul. 8, 2010, Office Action.
U.S. Appl. No. 12/403,277, Oct. 12, 2010, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 12/114,091, Oct. 27, 2010, Office Action.
U.S. Appl. No. 12/114,091, Jul. 7, 2011, Office Action.
U.S. Appl. No. 12/481,377, Jun. 21, 2011, Office Action.
U.S. Appl. No. 12/945,646, Jul. 6, 2011, Office Action.
U.S. Appl. No. 12/135,858, Jul. 13, 2011, Office Action.
U.S. Appl. No. 12/955,859, Jul. 21, 2011, Office Action.
U.S. Appl. No. 12/114,031, Aug. 2, 2011, Office Action.
U.S. Appl. No. 10/667,144, Jun. 6, 2011, Office Action.
U.S. Appl. No. 12/113,851, Apr. 27, 2011, Office Action.
U.S. Appl. No. 12/114,031, May 11, 2011, Office Action.
U.S. Appl. No. 12/143,020, May 11, 2011, Office Action.
U.S. Appl. No. 12/481,377, Apr. 28, 2011, Office Action.
U.S. Appl. No. 12/955,859, May 26, 2011, Office Action.
U.S. Appl. No. 13/308,227, filed Nov. 30, 2011, Yibarren.
U.S. Appl. No. 12/688,065, Apr. 26, 2012, Office Action.
U.S. Appl. No. 11/396,141, Apr. 30, 2013, Office Action.
U.S. Appl. No. 11/852,190, Apr. 24, 2013, Office Action.
U.S. Appl. No. 12/848,642, Apr. 26, 2013, Office Action.
U.S. Appl. No. 13/490,143, Apr. 29, 2013, Notice of Allowance.
U.S. Appl. No. 10/908,721, Jul. 18, 2013, Notice of Allowance.
U.S. Appl. No. 11/744,089, Aug. 8, 2013, Notice of Allowance.
U.S. Appl. No. 12/850,242, Aug. 6, 2013, Notice of Allowance.
U.S. Appl. No. 12/955,859, Aug. 1, 2013, Notice of Allowance.
U.S. Appl. No. 13/615,547, Aug. 7, 2013, Issue Notification.
U.S. Appl. No. 10/667,144, Oct. 28, 2011, Notice of Allowance.
U.S. Appl. No. 11/675,462, Dec. 22, 2011, Notice of Allowance.
U.S. Appl. No. 12/393,877, Sep. 29, 2011, Office Action.
U.S. Appl. No. 12/393,877, Dec. 13, 2011, Office Action.
U.S. Appl. No. 12/481,377, Jan. 3, 2012, Office Action.
U.S. Appl. No. 12/548,274, Dec. 28, 2011, Restriction Requirement.
U.S. Appl. No. 12/684,470, Dec. 20, 2011, Restriction Requirement.
U.S. Appl. No. 12/684,562, Dec. 28, 2011, Restriction Requirement.
U.S. Appl. No. 12/684,569, Dec. 20, 2011, Restriction Requirement.
U.S. Appl. No. 12/897,358, Jan. 12, 2012, Notice of Allowance.
U.S. Appl. No. 12/941,809, Dec. 13, 2011, Restriction Requirement.

(56) References Cited

OTHER PUBLICATIONS

U.S. Appl. No. 12/945,646, Oct. 26, 2011, Office Action.
U.S. Appl. No. 12/955,859, Dec. 15, 2011, Office Action.
U.S. Appl. No. 13/026,989, Sep. 16, 2011, Office Action.
U.S. Appl. No. 12/608,773, Jan. 7, 2013, Office Action.
U.S. Appl. No. 13/490,143, Jan. 4, 2013, Restriction Requirement.
U.S. Appl. No. 13/615,547, Jan. 18, 2013, Office Action.
U.S. Appl. No. 12/338,977, Jan. 19, 2012, Office Action.
U.S. Appl. No. 12/684,569, Jan. 27, 2012, Office Action.
U.S. Appl. No. 11/767,818, Feb. 3, 2012, Notice of Allowance.
U.S. Appl. No. 12/684,542, Jan. 30, 2012, Office Action.
U.S. Appl. No. 12/941,809, Jan. 30, 2012, Office Action.
U.S. Appl. No. 12/966,923, Feb. 3, 2012, Notice of Allowance.
U.S. Appl. No. 11/344,891, Jan. 22, 2013, Notice of Allowance.
U.S. Appl. No. 13/030,922, Jan. 31, 2013, Office Action.
U.S. Appl. No. 13/153,594, Jan. 29, 2013, Office Action.
U.S. Appl. No. 12/961,331, Feb. 1, 2013, Office Action.
U.S. Appl. No. 13/488,233, Feb. 5, 2013, Notice of Allowance.
U.S. Appl. No. 12/608,769, Feb. 10, 2012, Office Action.
U.S. Appl. No. 12/684,400, Feb. 13, 2012, Office Action.
U.S. Appl. No. 12/724,304, Feb. 10, 2012, Office Action.
U.S. Appl. No. 12/402,398, Mar. 13, 2013, Notice of Allowance.
U.S. Appl. No. 12/114,031, Mar. 6, 2012, Office Action.
U.S. Appl. No. 12/684,470, Mar. 23, 2012, Office Action.
U.S. Appl. No. 12/688,065, Mar. 13, 2012, Office Action.
U.S. Appl. No. 12/897,358, Mar. 5, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 12/338,977, Nov. 28, 2012, Office Action.
U.S. Appl. No. 12/961,331, Dec. 4, 2012, Office Action.
U.S. Appl. No. 13/030,922, Dec. 18, 2012, Office Action.
U.S. Appl. No. 10/667,144, Feb. 15, 2012, Issue Notification.
U.S. Appl. No. 12/135,858, Feb. 16, 2012, Office Action.
U.S. Appl. No. 12/684,562, Feb. 16, 2012, Office Action.
U.S. Appl. No. 12/945,646, Feb. 21, 2012, Notice of Allowance.
U.S. Appl. No. 13/791,829, filed Mar. 8, 2013, Roorda et al.
U.S. Appl. No. 13/791,846, filed Mar. 8, 2013, Palermo.
U.S. Appl. No. 13/112,618, Mar. 29, 2013, Office Action.
U.S. Appl. No. 13/112,631, Mar. 29, 2013, Office Action.
U.S. Appl. No. 13/308,227, Apr. 10, 2013, Office Action.
U.S. Appl. No. 13/525,839, Apr. 1, 2013, Office Action.
U.S. Appl. No. 11/744,089, Apr. 15, 2013, Office Action.
U.S. Appl. No. 12/850,242, Apr. 18, 2013, Office Action.
U.S. Appl. No. 13/052,634, Feb. 8, 2013, Office Action.
U.S. Appl. No. 13/052,634, Apr. 22, 2013, Office Action.
U.S. Appl. No. 13/615,547, Apr. 12, 2013, Notice of Allowance.
U.S. Appl. No. 11/390,586, May 3, 2012, Notice of Allowance.
U.S. Appl. No. 12/684,400, May 9, 2012, Office Action.
U.S. Appl. No. 12/897,358, May 2, 2012, Issue Notification.
U.S. Appl. No. 12/966,923, May 16, 2012, Issue Notification.
U.S. Appl. No. 13/898,202, filed May 20, 2013, Walberg et al.
U.S. Appl. No. 11/344,891, May 15, 2013, Issue Notification.
U.S. Appl. No. 12/955,859, May 16, 2013, Office Action.
U.S. Appl. No. 13/488,233, May 15, 2013, Issue Notification.
U.S. Appl. No. 11/390,586, Jul. 18, 2012, Issue Notification.
U.S. Appl. No. 12/608,773, Jul. 20, 2012, Office Action.
U.S. Appl. No. 12/684,569, Jul. 30, 2012, Office Action.
U.S. Appl. No. 13/039,087, Jul. 17, 2012, Office Action.
U.S. Appl. No. 13/525,839, Jun. 18, 2012, Carley et al.
U.S. Appl. No. 11/427,297, Jun. 26, 2012, Notice of Allowance.
U.S. Appl. No. 11/767,818, Jul. 4, 2012, Issue Notification.
U.S. Appl. No. 12/338,977, Jul. 11, 2012, Office Action.
U.S. Appl. No. 11/675,462, Aug. 16, 2012, Issue Notification.
U.S. Appl. No. 11/744,089, Aug. 8, 2012, Office Action.
U.S. Appl. No. 12/481,377, Aug. 10, 2012, Notice of Allowance.
U.S. Appl. No. 12/850,242, Aug. 6, 2012, Office Action.
U.S. Appl. No. 12/955,859, Aug. 6, 2012, Office Action.
U.S. Appl. No. 11/396,141, Aug. 21, 2013, Office Action.
U.S. Appl. No. 13/490,143, Aug. 21, 2013, Issue Notification.
U.S. Appl. No. 12/608,769, Aug. 22, 2012, Office Action.
U.S. Appl. No. 12/642,319, Aug. 28, 2012, Office Action.
U.S. Appl. No. 12/684,562, Aug. 21, 2012, Office Action.
U.S. Appl. No. 12/548,274, Sep. 10, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 12/987,792, Sep. 17, 2012, Office Action.
U.S. Appl. No. 10/786,444, Jul. 11, 2013, Notice of Allowance.
U.S. Appl. No. 11/532,325, Jul. 17, 2013, Office Action.
U.S. Appl. No. 13/030,922, Jul. 18, 2013, Office Action.
U.S. Appl. No. 13/525,839, Jul. 15, 2013, Notice of Allowance.
U.S. Appl. No. 13/615,547, Jul. 10, 2013, Issue Notification.
U.S. Appl. No. 13/153,594, May 29, 2013, Office Action.
U.S. Appl. No. 13/791,829, May 29, 2013, Office Action.
U.S. Appl. No. 12/143,020, May 30, 2012, Issue Notification.
U.S. Appl. No. 12/393,877, May 21, 2012, Office Action.
U.S. Appl. No. 12/941,809, Jun. 1, 2012, Office Action.
U.S. Appl. No. 12/945,646, May 30, 2012, Issue Notification.
U.S. Appl. No. 12/973,204, May 30, 2012, Issue Notification.
U.S. Appl. No. 11/427,309, Jun. 7, 2013, Notice of Allowance.
U.S. Appl. No. 13/112,618, Jun. 7, 2013, Office Action.
U.S. Appl. No. 13/488,233, Jun. 5, 2013, Issue Notification.
U.S. Appl. No. 12/608,773, Jun. 7, 2012, Office Action.
U.S. Appl. No. 13/026,989, Jun. 8, 2012, Office Action.
U.S. Appl. No. 12/338,977, Jun. 19, 2013, Office Action.
U.S. Appl. No. 11/344,891, Jun. 26, 2013, Issue Notification.
U.S. Appl. No. 12/402,398, Jun. 26, 2013, Issue Notification.
U.S. Appl. No. 13/112,631, Jun. 26, 2013, Office Action.
U.S. Appl. No. 11/427,297, Oct. 31, 2012, Issue Notification.
U.S. Appl. No. 12/114,091, Nov. 8, 2012, Office Action.
U.S. Appl. No. 12/403,277, Nov. 5, 2012, Office Action.
U.S. Appl. No. 12/608,769, Nov. 5, 2012, Notice of Allowance.
U.S. Appl. No. 12/684,400, Oct. 16, 2012, Office Action.
U.S. Appl. No. 12/848,642, Nov. 9, 2012, Office Action.
U.S. Appl. No. 12/850,242, Oct. 17, 2012, Office Action.
U.S. Appl. No. 13/039,087, Nov. 6, 2012, Notice of Allowance.
U.S. Appl. No. 12/106,928, Jun. 28, 2013, Office Action.
U.S. Appl. No. 12/106,937, Jun. 28, 2013, Office Action.
U.S. Appl. No. 12/941,809, Jul. 3, 2013, Office Action.
U.S. Appl. No. 12/961,331, Jul. 3, 2013, Office Action.
U.S. Appl. No. 12/114,091, Apr. 5, 2012, Office Action.
U.S. Appl. No. 12/684,542, Apr. 16, 2012, Office Action.
U.S. Appl. No. 12/143,020, Feb. 23, 2012, Notice of Allowance.
U.S. Appl. No. 12/548,274, Mar. 2, 2012, Office Action.
U.S. Appl. No. 12/642,319, Feb. 27, 2012, Office Action.
U.S. Appl. No. 12/113,851, Mar. 29, 2012, Office Action.
U.S. Appl. No. 12/403,277, Apr. 3, 2012, Office Action.
Turn—macmillandictionary.com/dictionary.american/turn.
Turn—Merriam-webster.com/dictionary/turn.
U.S. Appl. No. 11/411,925, Feb. 5, 2014, Notice of Allowance.
U.S. Appl. No. 11/455,993, Jan. 29, 2014, Office Action.
U.S. Appl. No. 11/532,325, Dec. 2, 2013, Office Action.
U.S. Appl. No. 11/852,190, Nov. 26, 2013, Office Action.
U.S. Appl. No. 11/852,190, Feb. 12, 2014, Notice of Allowance.
U.S. Appl. No. 12/106,928, Dec. 2, 2013, Office Action.
U.S. Appl. No. 12/106,937, Jan. 22, 2014, Office Action.
U.S. Appl. No. 12/403,277, Jan. 27, 2014, Office Action.
U.S. Appl. No. 12/642,319, Dec. 16, 2013, Office Action.
U.S. Appl. No. 12/848,642, Feb. 3, 2014, Notice of Allowance.
U.S. Appl. No. 12/941,809, Feb. 3, 2014, Notice of Allowance.
U.S. Appl. No. 12/987,792, Jan. 21, 2014, Office Action.
U.S. Appl. No. 13/030,922, Jan. 8, 2014, Notice of Allowance.
U.S. Appl. No. 13/112,618, Nov. 20, 2013, Office Action.
U.S. Appl. No. 13/112,631, Dec. 2, 2013, Office Action.
U.S. Appl. No. 13/791,829, Feb. 5, 2014, Issue Notification.
U.S. Appl. No. 13/898,202, Jan. 3, 2014, Office Action.
U.S. Appl. No. 13/222,899, Jan. 10, 2014, Office Action.
U.S. Appl. No. 14/017,039, filed Sep. 3, 2013, Ellingwood et al.
U.S. Appl. No. 14/023,428, filed Sep. 10, 2013, Ellingwood.
U.S. Appl. No. 10/908,721, Nov. 6, 2013, Issue Notification.
U.S. Appl. No. 11/396,141, Nov. 4, 2013, Notice of Allowance.
U.S. Appl. No. 11/411,925, Oct. 1, 2013, Office Action.
U.S. Appl. No. 12/688,065, Oct. 18, 2013, Office Action.
U.S. Appl. No. 12/941,809, Nov. 8, 2013, Office Action.

(56) References Cited

OTHER PUBLICATIONS

U.S. Appl. No. 12/955,859, Nov. 14, 2013, Issue Notification.
U.S. Appl. No. 12/961,331, Sep. 20, 2013, Advisory Action.
U.S. Appl. No. 13/026,989, Aug. 23, 2013, Office Action.
U.S. Appl. No. 13/052,634, Nov. 8, 2013, Office Action.
U.S. Appl. No. 13/153,594, Oct. 16, 2013, Notice of Allowance.
U.S. Appl. No. 13/308,227, Sep. 11, 2013, Office Action.
U.S. Appl. No. 13/525,839, Oct. 31, 2013, Issue Notification.
U.S. Appl. No. 13/791,829, Oct. 8, 2013, Notice of Allowance.
U.S. Appl. No. 12/402,398, Sep. 20, 2012, Office Action.
U.S. Appl. No. 12/688,065, Oct. 12, 2012, Office Action.
U.S. Appl. No. 12/848,642, Sep. 20, 2012, Office Action.
U.S. Appl. No. 14/246,926, filed Apr. 7, 2014, Carley et al.
U.S. Appl. No. 14/246,973, filed Apr. 1, 2014, Carley et al.
U.S. Appl. No. 11/113,549, Mar. 14, 2014, Notice of Allowance.
U.S. Appl. No. 11/674,930, Apr. 3, 2014, Notice of Allowance.
U.S. Appl. No. 12/106,928, Mar. 25, 2014, Advisory Action.
U.S. Appl. No. 12/113,851, Mar. 17, 2014, Office Action.
U.S. Appl. No. 12/114,031, Mar. 10, 2014, Office Action.
U.S. Appl. No. 12/684,569, Apr. 23, 2014, Office Action.
U.S. Appl. No. 12/688,065, Apr. 8, 2014, Office Action.
U.S. Appl. No. 12/950,628, Apr. 25, 2014, Notice of Allowance.
U.S. Appl. No. 12/961,331, Apr. 25, 2014, Notice of Allowance.
U.S. Appl. No. 14/323,753, filed Jul. 3, 2014, Fortson et al.
U.S. Appl. No. 11/113,549, Jul. 2, 2014, Issue Notification.
U.S. Appl. No. 11/411,925, Jun. 4, 2014, Issue Notification.
U.S. Appl. No. 11/852,190, Jun. 4, 2014, Issue Notification.
U.S. Appl. No. 11/958,295, Jun. 13, 2014, Notice of Allowance.
U.S. Appl. No. 12/608,773, Jul. 17, 2014, Office Action.
U.S. Appl. No. 12/642,319, May 27, 2014, Notice of Allowance.
U.S. Appl. No. 12/684,470, Jun. 4, 2014, Office Action.
U.S. Appl. No. 12/684,542, Jun. 18, 2014, Office Action.
U.S. Appl. No. 12/848,642, Jun. 4, 2014, Issue Notification.
U.S. Appl. No. 12/941,809, Jun. 4, 2014, Issue Notification.
U.S. Appl. No. 12/987,792, Jun. 11, 2014, Office Action.
U.S. Appl. No. 14/562,467, filed Dec. 5, 2014, Ellingwood et al.
U.S. Appl. No. 11/396,731, Feb. 12, 2015, Office Action.
U.S. Appl. No. 11/455,993, Aug. 11, 2014, Notice of Allowance.
U.S. Appl. No. 11/532,325, Jan. 16, 2015, Notice of Allowance.
U.S. Appl. No. 12/106,928, Oct. 3, 2014, Notice of Allowance.
U.S. Appl. No. 12/106,937, Mar. 5, 2015, Notice of Allowance.
U.S. Appl. No. 12/113,851, Aug. 21, 2014, Office Action.
U.S. Appl. No. 12/113,851, Feb. 20, 2015, Notice of Allowance.
U.S. Appl. No. 12/114,091, Feb. 12, 2015, Office Action.
U.S. Appl. No. 12/393,877, Aug. 4, 2014, Notice of Allowance.
U.S. Appl. No. 12/403,277, Aug. 15, 2014, Office Action.
U.S. Appl. No. 12/548,274, Aug. 14, 2014, Office Action.
U.S. Appl. No. 12/608,773, Mar. 12, 2015, Office Action.
U.S. Appl. No. 12/684,400, Feb. 23, 2015, Office Action.
U.S. Appl. No. 12/684,470, Nov. 14, 2014, Office Action.
U.S. Appl. No. 12/684,542, Dec. 1, 2014, Office Action.
U.S. Appl. No. 12/684,562, Sep. 10, 2014, Office Action.
U.S. Appl. No. 12/684,562, Feb. 17, 2015, Notice of Allowance.
U.S. Appl. No. 12/987,792, Aug. 25, 2014, Notice of Allowance.
U.S. Appl. No. 13/112,618, Dec. 15, 2014, Office Action.
U.S. Appl. No. 13/112,631, Nov. 20, 2014, Office Action.
U.S. Appl. No. 13/222,899, Jul. 31, 2014, Office Action.
U.S. Appl. No. 13/222,899, Apr. 1, 2015, Office Action.
U.S. Appl. No. 13/898,202, Aug. 21, 2014, Office Action.
U.S. Appl. No. 13/898,202, Feb. 10, 2015, Notice of Allowance.
U.S. Appl. No. 14/017,039, Jan. 23, 2015, Office Action.
U.S. Appl. No. 11/396,731, Jul. 9, 2015, Notice of Allowance.
U.S. Appl. No. 11/532,325, Jul. 8, 2015, Issue Notification.
U.S. Appl. No. 12/684,562, Jul. 8, 2015, Issue Notification.
U.S. Appl. No. 13/112,618, May 18, 2015, Office Action.
U.S. Appl. No. 13/112,631, Apr. 14, 2015, Office Action.
U.S. Appl. No. 13/791,846, Jun. 4, 2015, Office Action.
U.S. Appl. No. 14/017,039, Jun. 10, 2015, Office Action.
U.S. Appl. No. 14/466,576, Jul. 8, 2015, Office Action.
U.S. Appl. No. 14/732,977, filed Jun. 8, 2015, Walberg et al.
U.S. Appl. No. 14/839,658, filed Aug. 31, 2015, Cummins et al.
U.S. Appl. No. 14/855,080, filed Sep. 15, 2015, Voss et al.
U.S. Appl. No. 12/114,091, Mail Date Jul. 23, 2015, Office Action.
U.S. Appl. No. 12/684,400, Mail Date Jul. 28, 2015, Notice of Allowance.
U.S. Appl. No. 12/684,470, Mail Date Aug. 26, 2015, Office Action.
U.S. Appl. No. 13/222,899, Mail Date Aug. 5, 2015, Office Action.
U.S. Appl. No. 13/308,227, Mail Date Jul. 14, 2015, Office Action.
U.S. Appl. No. 13/908,796, Mail Date Jul. 21, 2015, Office Action.
U.S. Appl. No. 14/023,428, Mail Date Jul. 27, 2015, Office Action.
U.S. Appl. No. 14/077,007, Mail Date Jul. 27, 2015, Office Action.
U.S. Appl. No. 14/246,926, Mail Date Aug. 5, 2015, Office Action.
U.S. Appl. No. 14/246,973, Mail Date Aug. 3, 2015, Office Action.

* cited by examiner

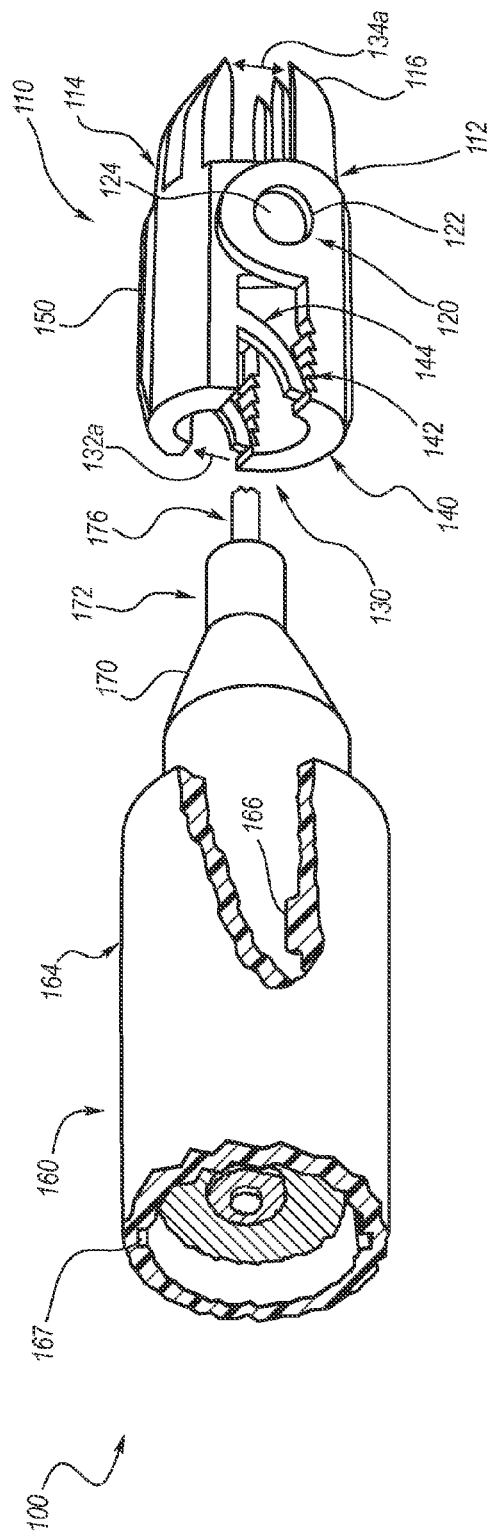
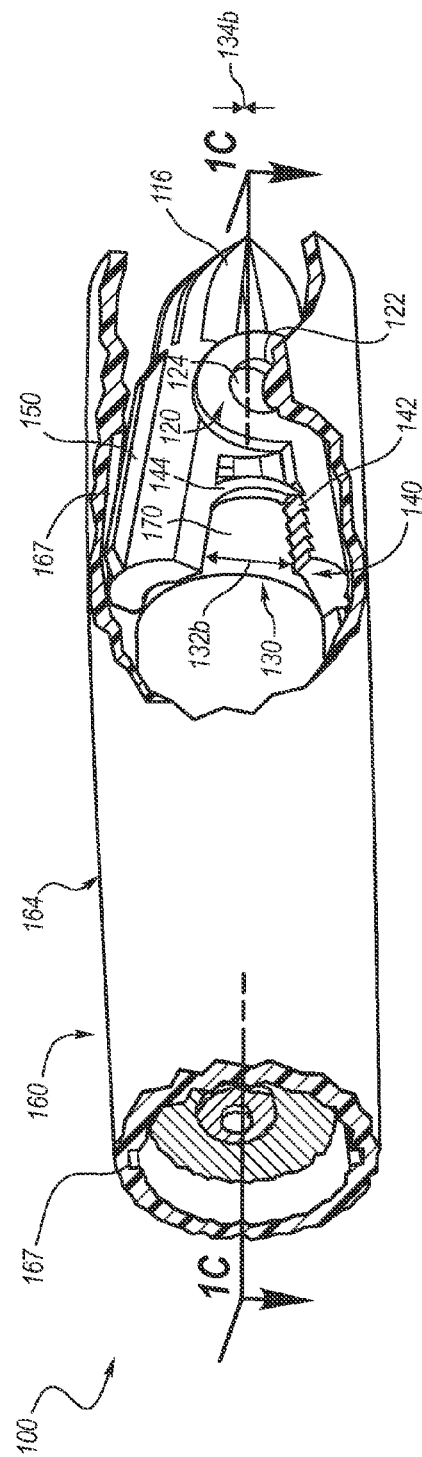
FIG. 1A
FIG. 1B

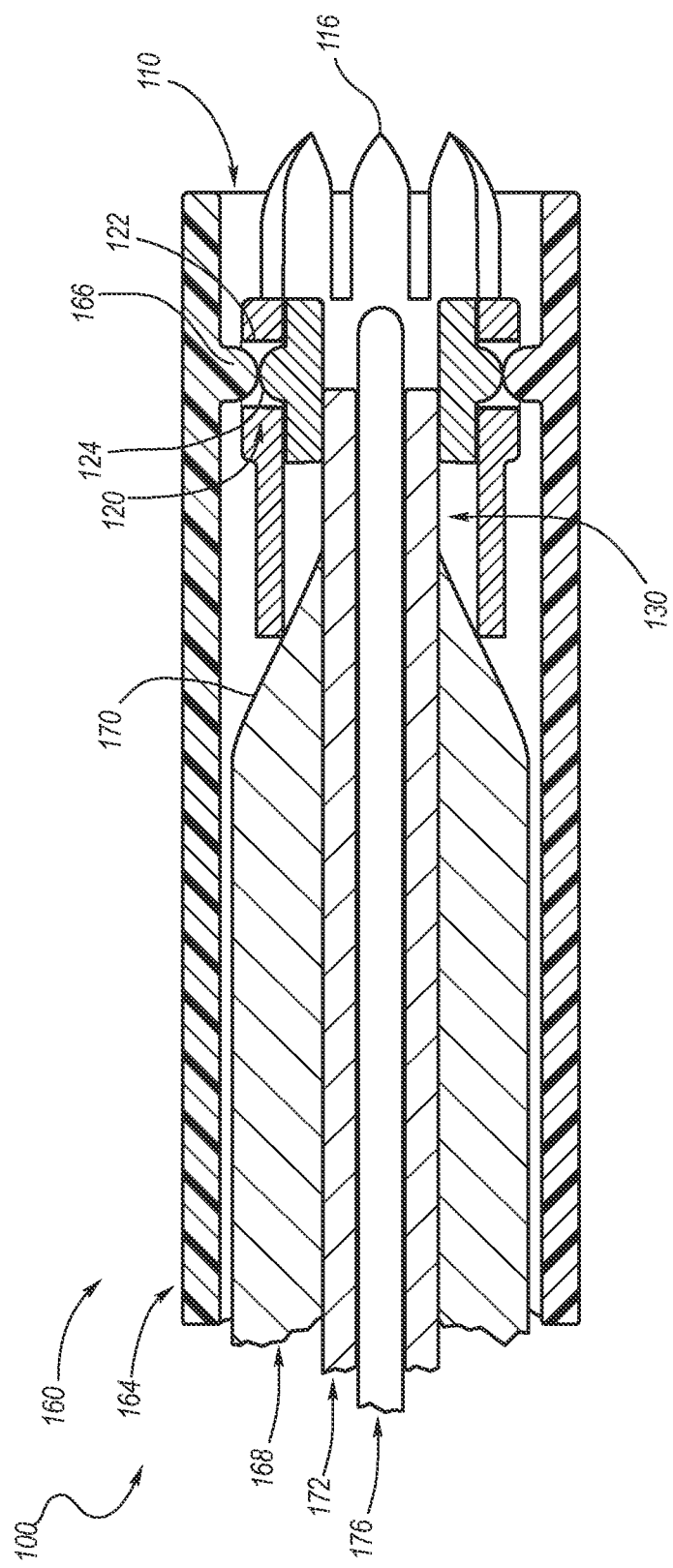

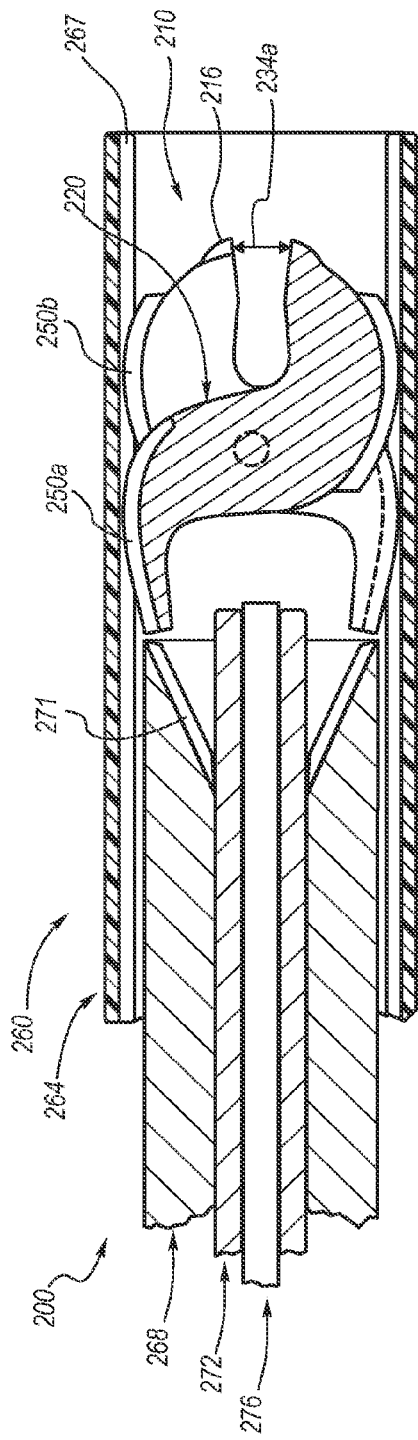
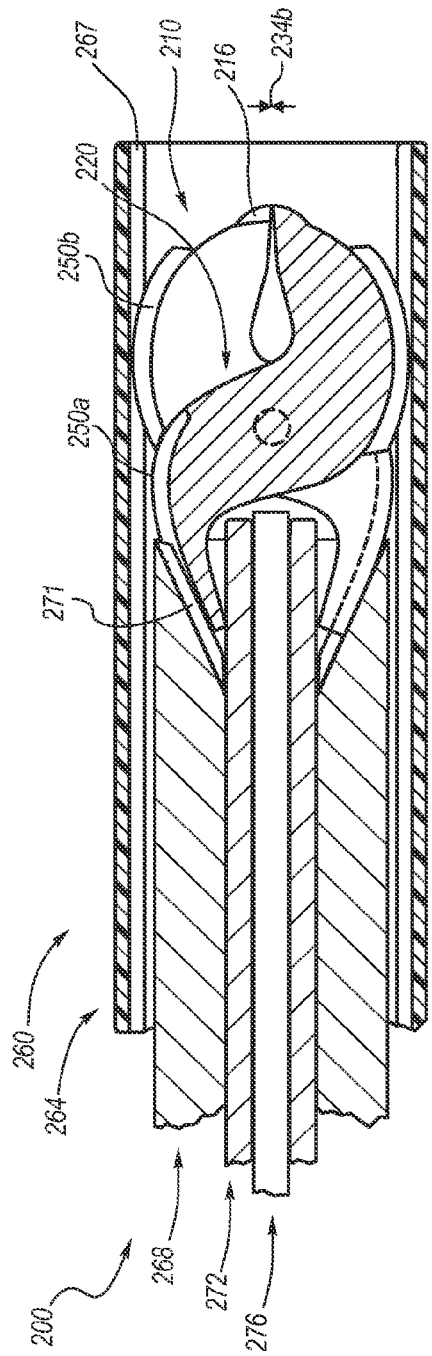
FIG. 2E
FIG. 2F

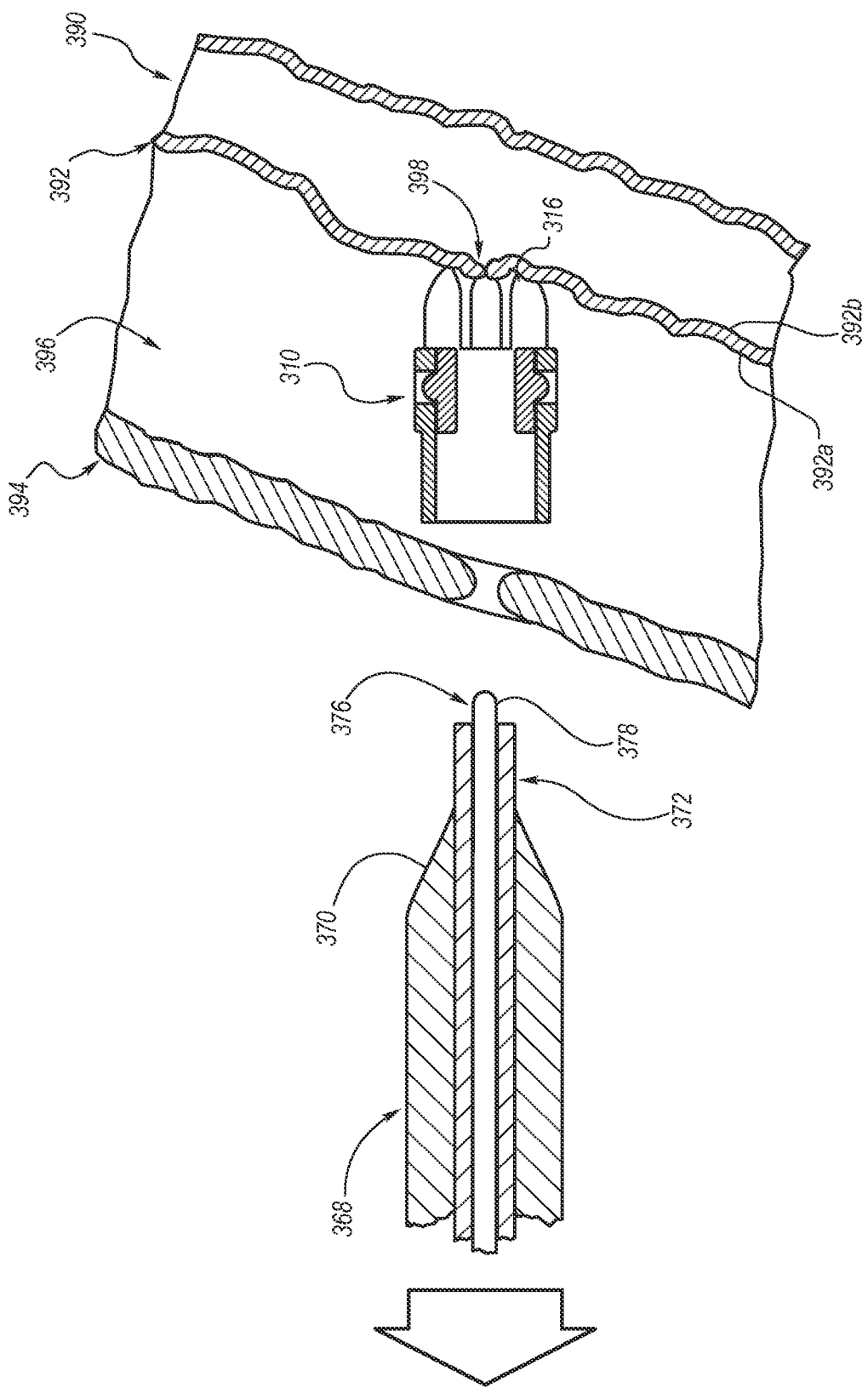

APPARATUS AND METHODS FOR ENGAGING TISSUE

FIELD OF THE INVENTION

The present invention relates generally to medical devices, and more particularly to apparatus and methods for engaging tissue.

BACKGROUND OF THE INVENTION

Catheterization and interventional procedures, such as angioplasty or stenting, generally are performed by inserting a hollow needle through a patient's skin and tissue into the vascular system. A guidewire may be advanced through the needle and into the patient's blood vessel accessed by the needle. The needle is then removed, enabling an introducer sheath to be advanced over the guidewire into the vessel, e.g., in conjunction with or subsequent to a dilator.

A catheter or other device may then be advanced through a lumen of the introducer sheath and over the guidewire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath are removed, leaving a puncture site in the vessel wall. Traditionally, external pressure had often been applied to the puncture site until clotting and wound sealing would occur; however, the patient must remain bedridden for a substantial period of time after clotting to ensure closure of the wound. This procedure, however, may be time consuming and expensive, requiring as much as an hour of a physician's or nurse's time. It is also uncomfortable for the patient and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,184, issued to Hathaway et al.

To facilitate positioning devices that are percutaneously inserted into a blood vessel, "bleed back" indicators have been suggested. For instance, U.S. Pat. No. 5,676,689, issued to Kensey et al., discloses a bleed back lumen intended to facilitate positioning of a biodegradable plug within a puncture site. This device, however, requires that an anchor of the plug be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand in order to engage the inner wall of the vessel, thereby facilitating holding the sheath in a desired location with respect to the vessel.

Accordingly, additional apparatus and methods for engaging tissue would be useful.

BRIEF SUMMARY

An embodiment of an engaging element for engaging tissue is described. The engaging element includes a first member having at least one tissue engaging portion. The engaging element includes a second member having at least one tissue engaging portion and being pivotally connected to the first member. The engaging element includes a locking mechanism that is operatively associated with the first and second member. The locking mechanism is configured to inhibit the relative motion of the first and second member.

An embodiment of an engaging system for engaging tissue is described. The engaging system includes an engaging element for engaging tissue. The engaging element includes a first member having at least one tissue engaging portion. The engaging element also includes a second member including at least one tissue engaging portion. The second member is pivotally connected to the first member. The engaging element further includes a locking mechanism operatively associated with the first and second member. The locking mechanism is configured to inhibit the relative motion of the first and second member. The engaging system also includes an engaging element delivery device. The engaging element delivery device includes a transitioning member. The transitioning member is configured to transition the engaging element from an open at configuration toward a closed configuration.

A method for engaging tissue is described. The method includes positioning an engaging element relative to an engaging element delivery device. The engaging element includes a first member having at least one tissue engaging portion. The engaging element also includes a second member having at least one tissue engaging portion. The second member is pivotally connected to the first member. The engaging element further includes a locking mechanism operatively associated with the first and second member. The locking mechanism is configured to inhibit the relative motion of the first and second member. The engaging element delivery device includes a retaining member. The retaining member includes a retaining mechanism and a transitioning member. The engaging element is positioned relative to a portion of tissue. A portion of the tissue is engaged with at least one tissue engaging portion. The engaging element is transitioned from an open configuration toward a closed configuration using the transitioning member. A locking mechanism is activated using the transitioning member to inhibit the relative motion of the first member and the second member.

In some embodiments of an engaging member, the first and second member include a proximal end. In further embodiments of an engaging member, the proximal ends of the first member and second member are separated by a first transitioning dimension in an open configuration and a second transitioning dimension in a closed configuration.

The first transitioning dimension, in some embodiments of an engaging member, is larger than said second transitioning dimension. In other embodiments of an engaging member, the first transitioning dimension is smaller than said second transitioning dimension. In further embodiments of an engaging member, the locking mechanism includes a first locking portion and a second locking portion, such that movement of the at least one tissue engaging portions of the first and second members is inhibited by the operative association between the first and second locking portions.

In some embodiments of an engaging member, the first locking portion includes at least one tooth associated with the first member and the second locking portion includes a locking member associated with the second member. In other embodiments of an engaging member, the locking member is biased toward the at least one tooth.

The locking member and the at least one tooth, in some embodiments of an engaging member, inhibit the at least one tissue engaging portions of the first and second members from moving toward the open configuration. In further embodiments of an engaging member, the first locking portion includes a latch associated with the first member and the second locking portion includes a latching portion associated with the second member. In still further embodiments of an engaging member, the latch and the latching portion inhibit the at least one tissue engaging portion of the first and second members from moving toward the open configuration.

In some embodiments of an engaging member, at least one tissue engaging portion of the first member and the at least one tissue engaging portion of the second member are separated by a first distal dimension in an open configuration and are separated by a second distal dimension in a closed configuration. The first distal dimension is larger than the second distal dimension, in some embodiments of an engaging member.

The engaging element, in some embodiments, includes a pivoting mechanism operatively associated with the first and the second members. In further embodiments of an engaging member, the pivoting mechanism includes a pivoting opening associated with one of the first member and the second member and a pivoting member associated with the other of the first member and the second member.

In some embodiments of an engaging member, the engaging element further comprises a retaining portion configured to be operatively associated with a retaining mechanism. In further embodiments of an engaging member, the engaging element includes bioabsorbable, biodegradable, and/or bio-erodible material. In still further embodiments, the engaging element includes collagen, polycaprolactone (PCL), poly-D, L-lactic acid, Poly-L-lactic acid, poly(lactide-co-glycolide), poly(hydroxybutyrate), polyanhydrides, and/or poly(glycolic acid).

The engaging element, in some embodiments of an engaging system, includes a pivoting mechanism operatively associated with said first and said second member. Further embodiments of an engaging system include a retaining member that has a retaining mechanism configured to selectably inhibit the relative motion of said engaging element and said retaining member.

In some embodiments of an engaging system, a pivoting mechanism includes a pivoting opening associated with one of the first and second member and a pivoting member associated with the other of the first and second member. In further embodiments of an engaging system, the retaining mechanism is operatively associated with the pivoting opening to selectably inhibit the relative motion of the engaging element and the retaining member. In still further embodiments of an engaging system, the retaining mechanism includes a retaining detent that engages the pivoting opening to selectably inhibit the relative motion of the engaging element and the retaining member.

The retaining member and the transitioning member, in some embodiments of an engaging system, are axially aligned. In further embodiments of an engagement system, the retaining member is configured to slidably receive the transitioning member.

In some embodiments of an engaging system, the first and second member of the engaging element include a transitioning portion. The transitioning member, in further embodiments, includes a transitioning surface that is shaped to engage with the transitioning portion of at least one of the first and second member of the engaging element. In some embodiments, the transitioning surface has a convex shape. In other embodiments, the transitioning surface has a concave shape.

Some embodiments of a method for engaging tissue include selectably retaining the engaging element using a retaining mechanism to inhibit the relative motion of the engaging element and the retaining member. Further embodiments of a method for engaging tissue include disengaging the locking mechanism.

Other aspects and features of the present invention will become apparent from consideration of the following description in conjunction with the accompanying drawings.

BRIEF DESCRIPTION OF THE DRAWINGS

In order to describe the manner in which the above-recited and other advantages and features of the invention can be obtained, a more particular description of the invention will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

FIG. 1A is a perspective partial cutaway view of an embodiment of a system for engaging tissue with an engaging element in an open configuration, according to an embodiment of the present invention.

FIG. 1B is a perspective partial cutaway view of the embodiment of a system for engaging tissue of FIG. 1A with an engaging element in a closed configuration, according to the present invention.

FIG. 1C is a top cutaway view of the embodiment of the system for engaging tissue of FIG. 1A, according to the present invention.

FIG. 2E is a right cutaway view of the embodiment of the system for engaging tissue of FIG. 2C with the embodiment of the engaging element of FIG. 2A in an open configuration, according to the present invention.

FIG. 2F is a right cutaway view of the embodiment of the system for engaging tissue of FIG. 2C with the embodiment of the engaging element of FIG. 2A in a closed configuration, according to the present invention.

FIGS. 3A-3K illustrate various steps in the deployment of an embodiment of an engaging element to engage tissue according to one example.

Figure 2A:
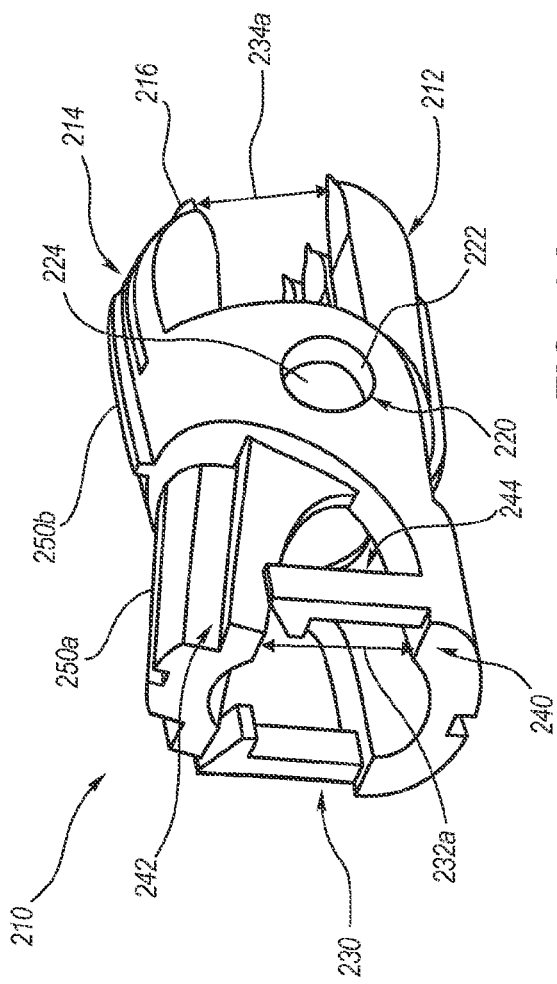
FIG. 2A is a perspective view of another embodiment of an engaging element in an open configuration, according to the present invention.

It should be noted that the figures are not drawn to scale and that elements of similar structures or functions are generally represented by like-reference numerals for illustrative purposes throughout the figures. It also should be noted that the figures are only intended to facilitate the description of embodiments of the present invention.

DETAILED DESCRIPTION

Embodiments described herein extend to methods, systems, and apparatus for engaging tissue. Some embodiments may be used to close and/or seal openings in a blood vessel or other body lumen formed during a diagnostic, therapeutic, and/or other procedure. The engaging elements of the present invention may be configured to be delivered through tissue and into an opening formed in and/or adjacent to a wall of a blood vessel or other body lumen. The engaging elements provided herein may reliably engage.

Moreover, the engaging elements may be made of any suitable material, including a bioabsorbable material, such as collagen. Other biodegradable materials may include polycaprolactone (PCL), poly-D,L-lactic acid, Poly-L-lactic acid, poly (lactide-co-glycolide), poly(hydroxybutyrate), polyanhydrides, poly(glycolic acid, and/or other biodegradable materials.

Referring generally to FIGS. 1A-1C, the system 100 may include an engaging element 110 and an engaging element delivery device 160. The engaging element 110 may include a first member 112 and a second member 114. The first member 112 and the second member 114 may include tissue engaging portions 116 (three tissue engaging portions 116 on each of the first member 112 and the second member 114, in the present at embodiment). The tissue engaging portions 116 may include a sharpened tip, as shown, and/or may include other tips, such as barbed tips. The tissue engaging portions 116 may be configured to engage tissue.

The engaging element delivery device 160 may include a retaining member 164, a transitioning member 168, a carrier member 172, a locator 176, and/or other components. The transitioning member 168 may include a lumen. The lumen may receive the carrier member 172, the locator 176, and/or other components. The carrier member 172 may be configured to receive a locator 176 and/or other components.

The engaging element 110, locator 176, carrier member 172, transitioning member 168, and/or retaining member 164 may be axially aligned. The carrier member 172 and/or locator 176 may be configured to fit within a channel of the engaging element 110 in the open configuration.

The first member 112 and second member 114 may be pivotally connected. The first member 112 and second member 114 may be pivotally connected by a pivoting mechanism 120. The pivoting mechanism 120 may include a pivoting opening 122 and a pivoting member 124. The pivoting member 124 may be located on the first member 112 and the pivoting opening 122 may be located on the second member 114. Alternatively, the pivoting member 124 and pivoting opening 122 may be located on either the first member 112 or the second member 114. Other pivoting mechanisms 120 may also be used. The pivoting member 124 of the present embodiment may include a detent configured to engage the pivoting opening 122.

The engaging element 110 may include a transitioning portion 130 with a first transitioning dimension 132a, in the open configuration shown in FIG. 1A, and a second it transitioning dimension 132b in the closed configuration shown in FIG. 1B. Transitioning dimensions 132a, 132b may indicate distances between the first member 112 and the second member 114 in various configurations. The first transitioning dimension 132a may be smaller than the second transitioning dimension 132b.

The engaging element 110 may include a first distal dimension 134a in the open configuration and a second distal dimension 134b in the closed configuration. Distal dimensions 134a, 134b may indicate distances between the first member 112 and the second member 114 in various configurations. The first distal dimension 134a may be larger than the second transitioning dimension 132b.

The transitioning portion 130 may be configured to receive a distal end of the transitioning member 168. The transitioning member 168 may include a transitioning surface 170 located near the distal end. The transitioning member 168 may be elongate and/or convex. The transitioning surface 170 may be operatively associated with the transitioning portion 130 of the engaging element 110 to transition the engaging element 110 from the open configuration toward the closed configuration.

Referring to FIGS. 1A and 1B, transitioning the engaging element 110 from the open configuration toward the closed configuration may include expanding the first transitioning dimension 132a toward the second transitioning dimension 132b. As the transitioning surface 170 of the transitioning member 168 engages the transitioning portion 130 of the engaging element 110, the proximal ends of the first member 112 and second member 114 may expand away from each other. As the proximal ends expand away from each other (from the open configuration), the tissue engaging portions 116 of at the first member 112 and the second member 114 may move toward each other (toward the closed configuration).

The engaging element 110 may include a locking mechanism 140 that may be configured to generally inhibit movement from the closed configuration towards the open configuration. For example, as the proximal ends expand away from each other, the locking mechanism 140 may inhibit movement back toward the open configuration.

The locking mechanism 140 may include a first locking portion 142 and a second locking portion 144. The first locking portion 142 and the second locking portion 144 may be operatively associated. The first locking portion 142 and/or the second locking portion 144 may be located near the proximal ends of the first member 112 and/or the second member 114, respectively. The first locking portion 142 may include at least one tooth. The at least one tooth may be configured to receive the second locking portion 144 which may include a locking member such as a follower. The locking member may be biased toward the at least one tooth. The use of multiple teeth may incrementally inhibit movement toward the open configuration.

The pivoting opening 122 may include a retaining portion. The pivoting opening 122 may be configured to receive at least a portion of a retaining mechanism 166 on the retaining member 164 and the pivoting member 124 of the engaging element 110. The pivoting opening 122 and retaining mechanism 166 may be operatively associated to limit movement of the engaging element 110 in at least one direction. For instance, the pivoting opening 122 and retaining mechanism 166 may limit motion of the engaging element 110 both longitudinally (i.e. through the retaining member 164) and radially (i.e. at about an axis within the retaining member 164). The engaging element 110 may be inserted through the retaining member 164 until the retaining mechanism 166 and the pivoting opening 122 are retained. Alternatively, the retaining portion may be located on the retaining member 164 while the retaining mechanism 166 is located on the engaging element 110. Other retaining portion and/or retaining mechanism combinations, such as a detent and retaining groove combination, may be used.

In order to align the pivoting opening 122 of the engaging element 110 with the retaining mechanism 166 of the retaining member 164, the engaging element 110 may include an aligning portion 150, as shown in FIGS. 1A and 1B, which may be operatively associated with an aligning mechanism 167 of the retaining member 164. The aligning portion 150 of the engaging element 110 may include a ridge configured to be inserted into the aligning mechanism 167 (i.e. a corresponding slot or groove) of the retaining member 164. In another embodiment, the aligning portion 150 of the engaging element 110 may be a slot or groove configured to receive the aligning mechanism 167, i.e. ridge, tab, etc., of the retaining member 164. In further embodiments, the aligning portion 150 and/or the aligning mechanism 167 may take other forms to align the engaging element 110 with the retaining member 164 and/or transitioning member 168.

Referring to FIGS. 2A-2F, the system 200 and engaging element 210 of this embodiment may be at least partially functionally similar to that of the system 100 and engaging element 210 previously described above and shown in FIG. 1 in most respects, wherein certain features will not be described in relation to this embodiment wherein those components may function in the manner as described above and are hereby it incorporated into this alternative embodiment described below. Like structures and/or components are given like reference numerals.

The engaging element 210 may include a first member 212 and a second member 214. The first member 212 and the second member 214 may be configured to engage tissue. The tissue engaging portions 216 may include tissue engaging portions 216 that may include a sharpened tip, barb, and/or other tip.

The first member 212 and second member 214 may be pivotally connected by a pivoting mechanism 220. The pivoting mechanism 220 may include a pivoting opening 222 and a pivoting member 224. The pivoting opening 222 may be located on the first member 212 and the pivoting member 224 may be located on the second member 214.

Figure 2B:
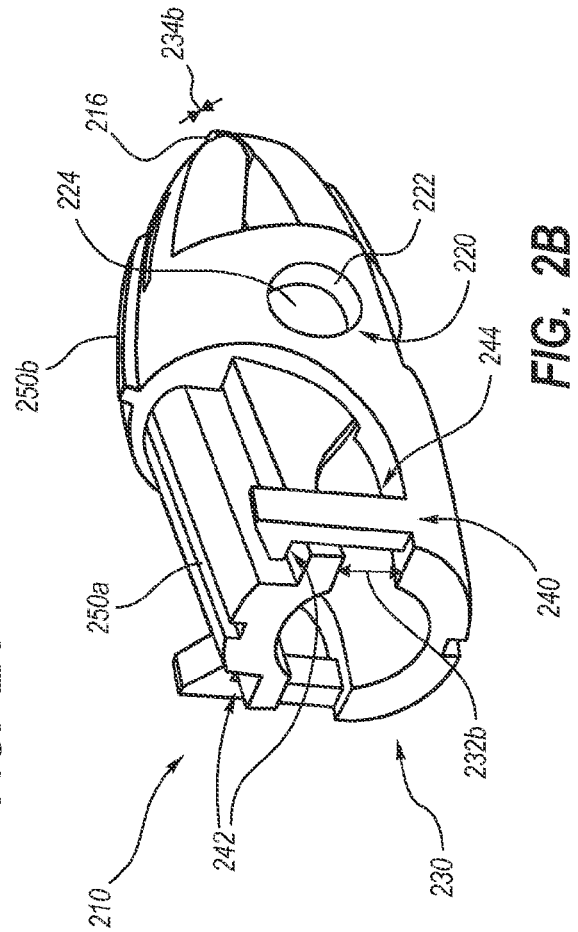
FIG. 2B is a perspective view of the embodiment of the engaging element of FIG. 2A in a closed configuration, according to the present invention.

The engaging element 210 may include a transitioning portion 230 with a first transitioning dimension 232a, in the open configuration shown in FIG. 2A, and a second transitioning dimension 232b in the closed configuration shown in FIG. 2B. The first transitioning dimension 232a may be larger than the second transitioning dimension 232b.

The engaging element 210 may include a first distal dimension 234a in the open configuration and a second distal dimension 234b in the closed configuration. The first distal dimension 134a may be larger than the second transitioning dimension 232b.

Figure 2C:
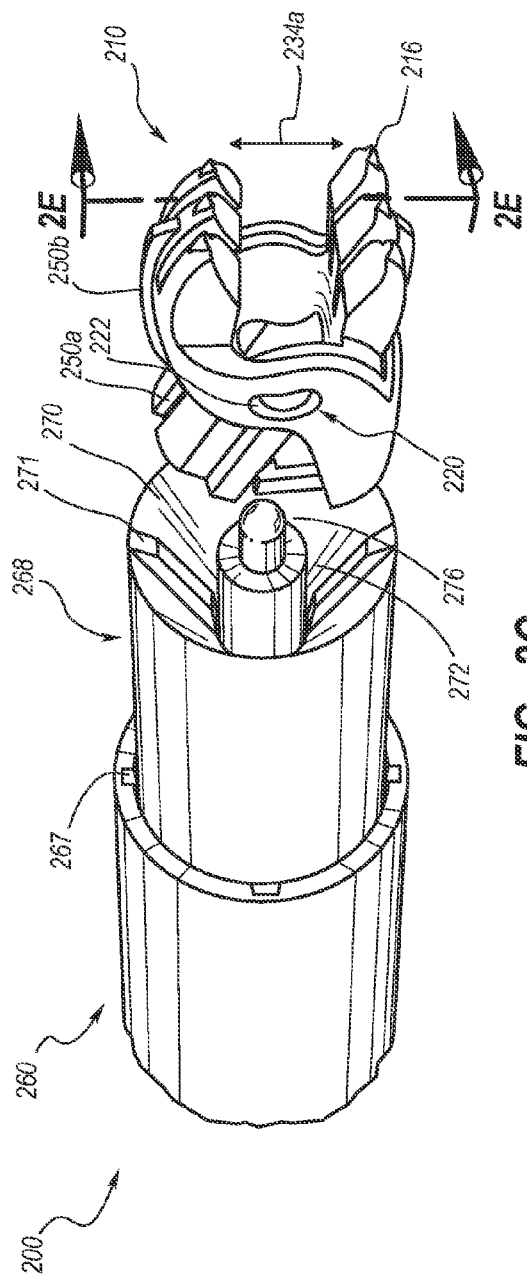
FIG. 2C is a perspective view of an embodiment of a system for engaging tissue with the embodiment of the engaging element of FIG. 2A in an open configuration, according to the present invention.
Figure 2D:
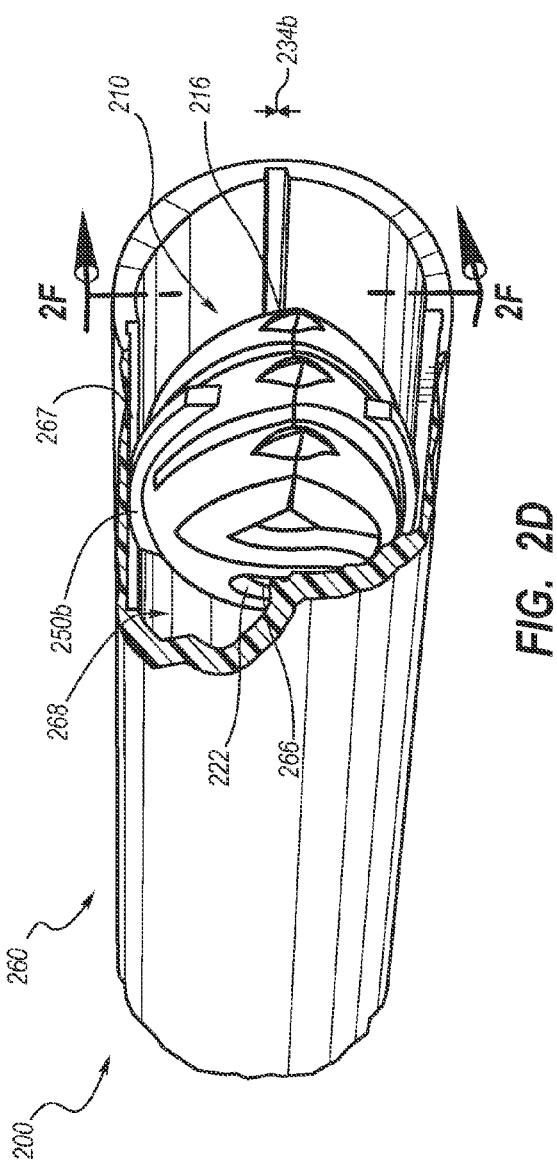
FIG. 2D is a perspective partial cutaway view of the embodiment of a system for engaging tissue of FIG. 2C with the embodiment of the engaging element of FIG. 2A in a closed configuration, according to the present invention.

Referring to the system 200 shown in FIGS. 2C-2D, the engaging element delivery device 260 may include a transitioning member 268, a retaining member 264, a carrier member 272, a locator 276, and/or other components. The transitioning at portion 230 of the engaging element 210 may be configured to receive a distal end of the transitioning member 268. The transitioning member 268 may include a transitioning surface 270 located near the distal end that may be concave. The transitioning surface 270 may be operatively associated with the transitioning portion 230 of the engaging element 210 to transition the engaging element 210 from the open configuration toward the closed configuration.

Referring to FIGS. 2C-2F, transitioning the engaging element 210 from the open configuration toward the closed configuration may include moving the first transitioning dimension 232a toward the second transitioning dimension 232b. As the transitioning surface 270 of the transitioning member 268 engages the transitioning portion 230 of the engaging element 210, the proximal ends of the first member 212 and second member 214 may move toward each other. As the proximal ends move toward each other (from the open configuration), the tissue engaging portions 216 of the first member 212 and the second member 214 may also move toward each other (toward the closed configuration).

The engaging element 210 may include a locking mechanism 240 that may be configured to generally inhibit movement from the closed configuration towards the open configuration. For example, as the proximal ends move toward each other the locking mechanism 240 may inhibit movement toward the open configuration.

The locking mechanism 240 may include a first locking portion 242 and a second locking portion 244. The first locking portion 242 and the second locking portion 244 may be operatively associated. The first locking portion 242 and/or the at second locking portion 244 may be located near the proximal ends of the first member 212 and/or the second member 214, respectively. The first locking portion 242 may include a latch member. The latch member may be configured to engage the second locking portion 244 which may include a latching portion. The latch member may be biased to engage the latching portion. Although the latch member and latching portion may be located on the first member 212 and the second member 214, respectively, other locations may also be used. Furthermore, although a locking member and tooth combination and a latch member and latching portion combination have been described, other locking mechanisms may be used. For instance, a set of interlocking teeth may be disposed on the first member 212 and the second member 214 similar to the locking mechanism used for locking forceps.

The pivoting opening 222 may include a retaining portion that may be configured to receive a retaining mechanism 266 on the retaining member 264. The pivoting opening 222 and retaining mechanism 266 may be operatively associated to limit movement of the engaging element 210 in at least one direction.

The engaging element 210 of the present embodiment may include two types of aligning portions 250a, 250b. The aligning portions 250a near the proximal end of the engaging element 210 may be grooves configured to receive an aligning mechanism 271 (i.e. a ridge) on the transitioning member 268. The aligning portions 250b near the tissue engaging portions 216 may be ridges configured to be inserted into a first aligning mechanism 267, i.e. a corresponding slot or groove, of the retaining member 264. Other alignment portions 250a, 250b, alignment mechanisms 267, 271, and/or configurations of the same (i.e. alignment portions and/or alignment mechanisms on the engaging at element 210, retaining member 264, transitioning member 268, and/or other components) may be used to orient the engaging element 210 relative to the engaging element delivery device 260 such that the retaining member 264 may retain the engaging element 210.

The transitioning member 268 may include a lumen that may receive a carrier member 272, a locator 276, and/or other components. The carrier member 272 may be configured to receive a locator 276 and/or other components.

The transitioning member 268 may abut the transitioning portion 230 of the engaging element 210. The transitioning member 268 may include a transitioning surface 270 that is concave. As the transitioning member 268 is advanced through the retaining member 264, the transitioning member 268 may transition the engaging member 210 toward a closed configuration. The concave transitioning surface 270 may generally cause the proximal ends of the first member 212 and the second member 214 to move toward each other. As the proximal ends of the first member 212 and the second member 214 move toward each other, the tissue engaging portions 216 on the first member 212 and the second member 214 may move toward each other.

FIGS. 3A-3K illustrate various steps in the deployment of an embodiment of an engaging element 310 to close a puncture according to one example. The systems 100, 200 and engaging elements 110, 210 discussed above in connection with FIGS. 1A-1C and 2A-2F will now be discussed in the context of a patient and with respect to a blood vessel 390. The systems 100, 200 and engaging elements 110, 210 may also be used with body lumens other than blood vessels.

The system 300 and engaging element 310 of this embodiment may be at least partially functionally similar to that of the systems 100, 200 and engaging elements 110, 210 previously described above and shown in FIGS. 1 and 2 in most respects, wherein certain features will not be described in relation to this embodiment wherein those components may function in the manner as described above and are hereby incorporated into this alternative embodiment described below. Like structures and/or components are given like reference numerals.

The blood vessel 390 has a vessel wall 392 with an outer portion 392a and an inner portion 392b. The engaging element delivery device 360 may then be used to apply the engaging element 310. In particular, a sheath 380 may be inserted or otherwise positioned through skin 394 and tissue 396 and within the blood vessel 390 or other body lumen via an opening 398. The sheath 380 can include a substantially flexible or semi-rigid tubular member. Also, the sheath 380 can have a proximal end region 382a and a distal end region 382b. The sheath 380 may further have a predetermined length and a predetermined cross-section, both of which can be of any suitable dimension. The sheath 380 also can form a lumen 384 that extends along a longitudinal axis of the sheath 380 and substantially between the proximal and distal end regions 382a, 382b. The lumen 384 can have any suitable internal cross-section and is suitable for receiving one or more devices (not shown), such as a guidewire 388, a catheter, and/or other devices.

The sheath 380 may be advanced over a guidewire 388 and/or other rail that may have been positioned through the opening 398 and into the blood vessel 390 using conventional procedures. The blood vessel 390 can be a peripheral blood vessel, such as a femoral or carotid artery, although other body lumens may be accessed using the sheath 380. The opening 398, and consequently the sheath 380, may be oriented with respect to the blood vessel 390 such as to facilitate the introduction of devices through the lumen 384 of the sheath 380 and into the blood vessel 390 with minimal risk of damage to the blood vessel 390. One or more devices (not shown), such as a catheter, or the like, may be inserted through the sheath 380 and advanced to a preselected location within the patient's body. For example, the devices may be used to perform a therapeutic and/or diagnostic procedure, such as angioplasty, atherectomy, stent implantation, and the like, within the patient's vasculature.

Figure 3A:
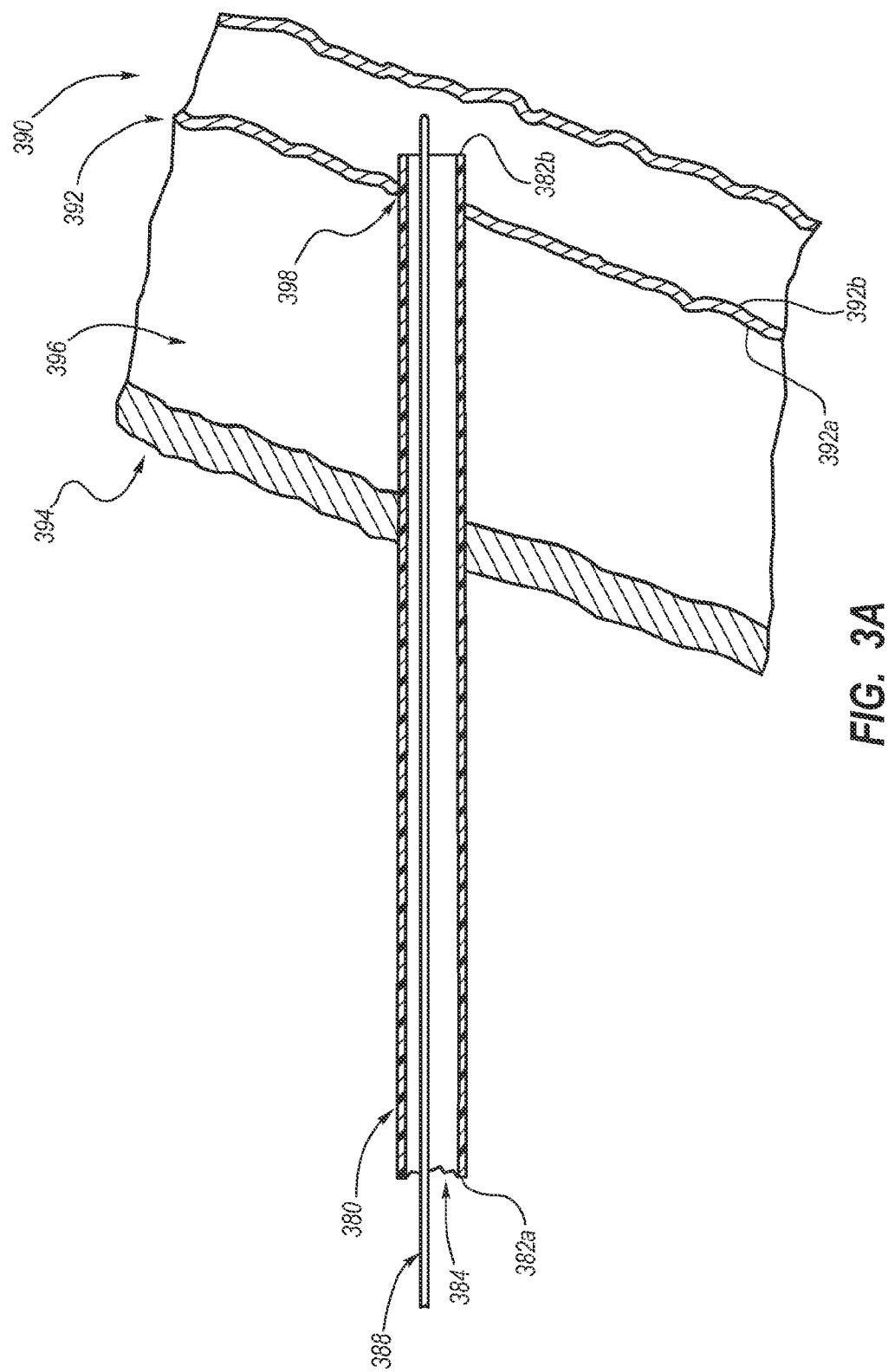
Figure 3B:
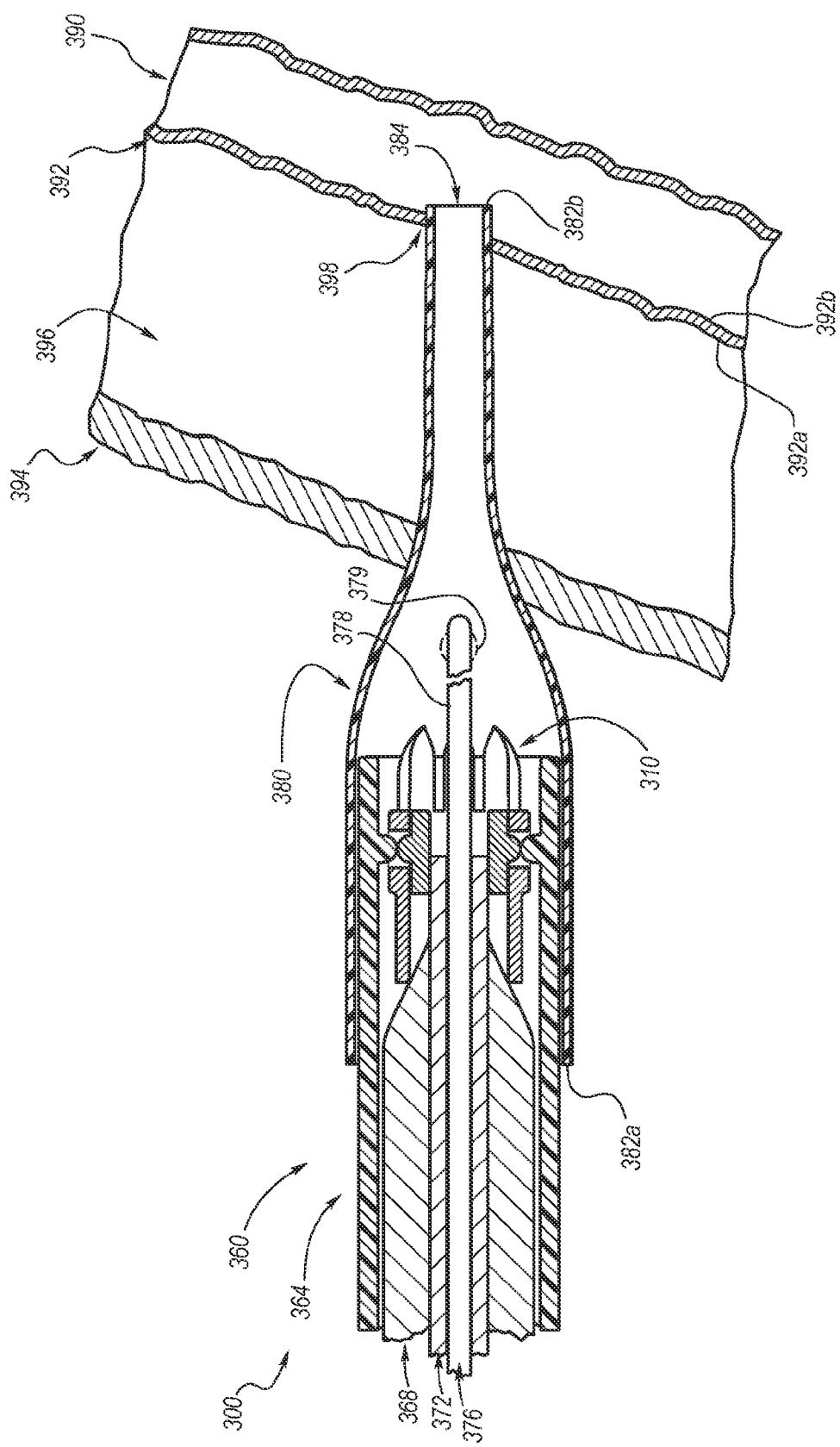

After the procedure is completed, the devices may be removed from the sheath 380. The engaging element delivery device 360 may be prepared to be received by the lumen 384 of the sheath 380 as shown in FIG. 3B. Alternatively, the sheath 380 may be removed and then the engaging element delivery device 360 may be positioned near the opening 398. The engaging element delivery device 360 may include a retaining member 364, a transitioning member 368, a carrier member 372, a locator 376, and/or other components. The carrier member 372 may provide support for the engaging element 310. The locator 376 may be inserted through a channel in the carrier member 372.

Figure 3C:
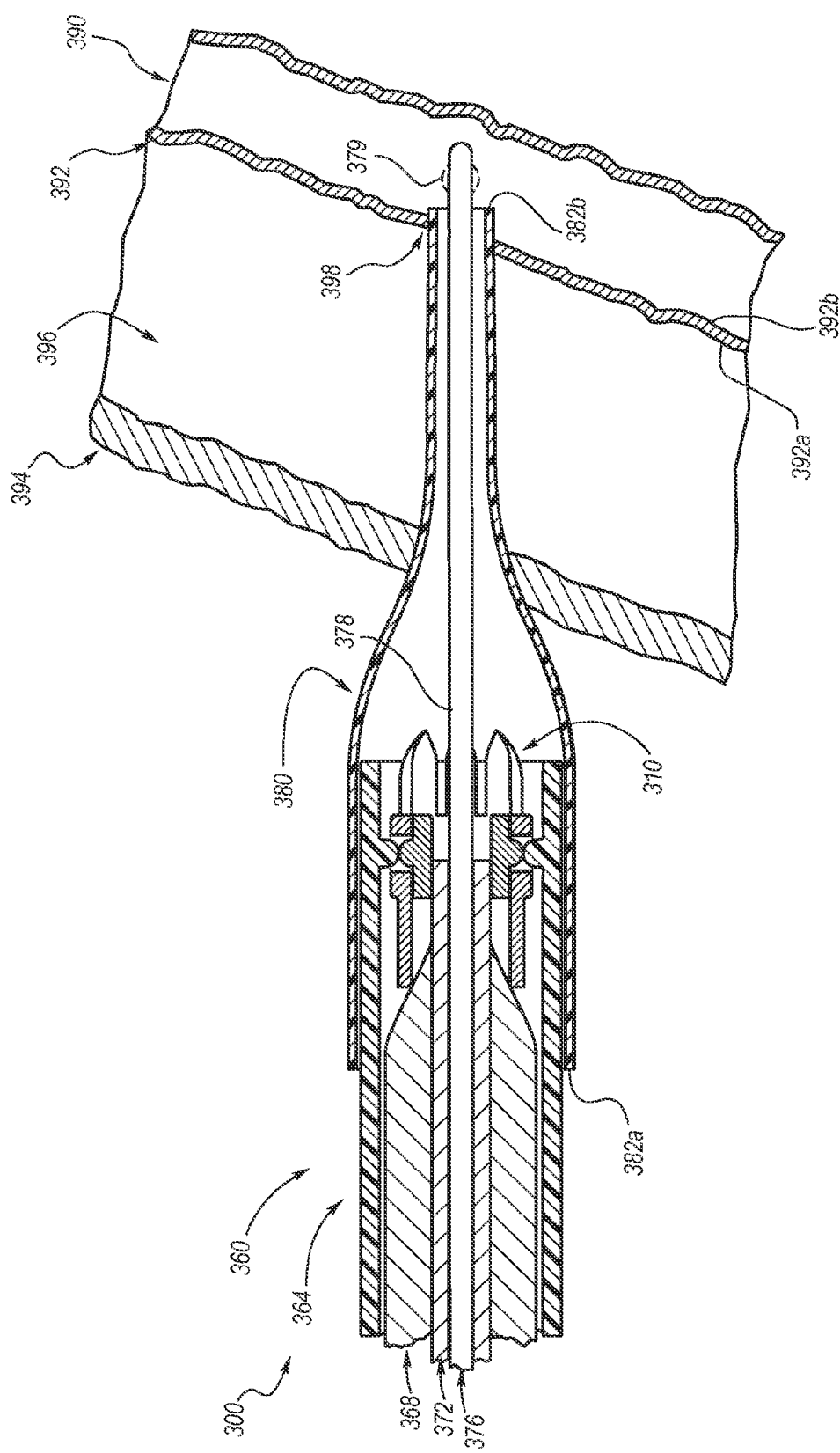

The locator 376 may include a tubular body 378 having a distal end region 379. Being in the unexpanded state, the distal end region 379 of the tubular body 378 of the locator 376 can be slidably received by the lumen 384 and atraumatically advanced distally into the blood vessel 390 as illustrated in FIGS. 3B-3C. Advancing the distal end region 379 into the lumen 384 begins the location of the locator 376 relative to the blood vessel 390.

Figure 3D:
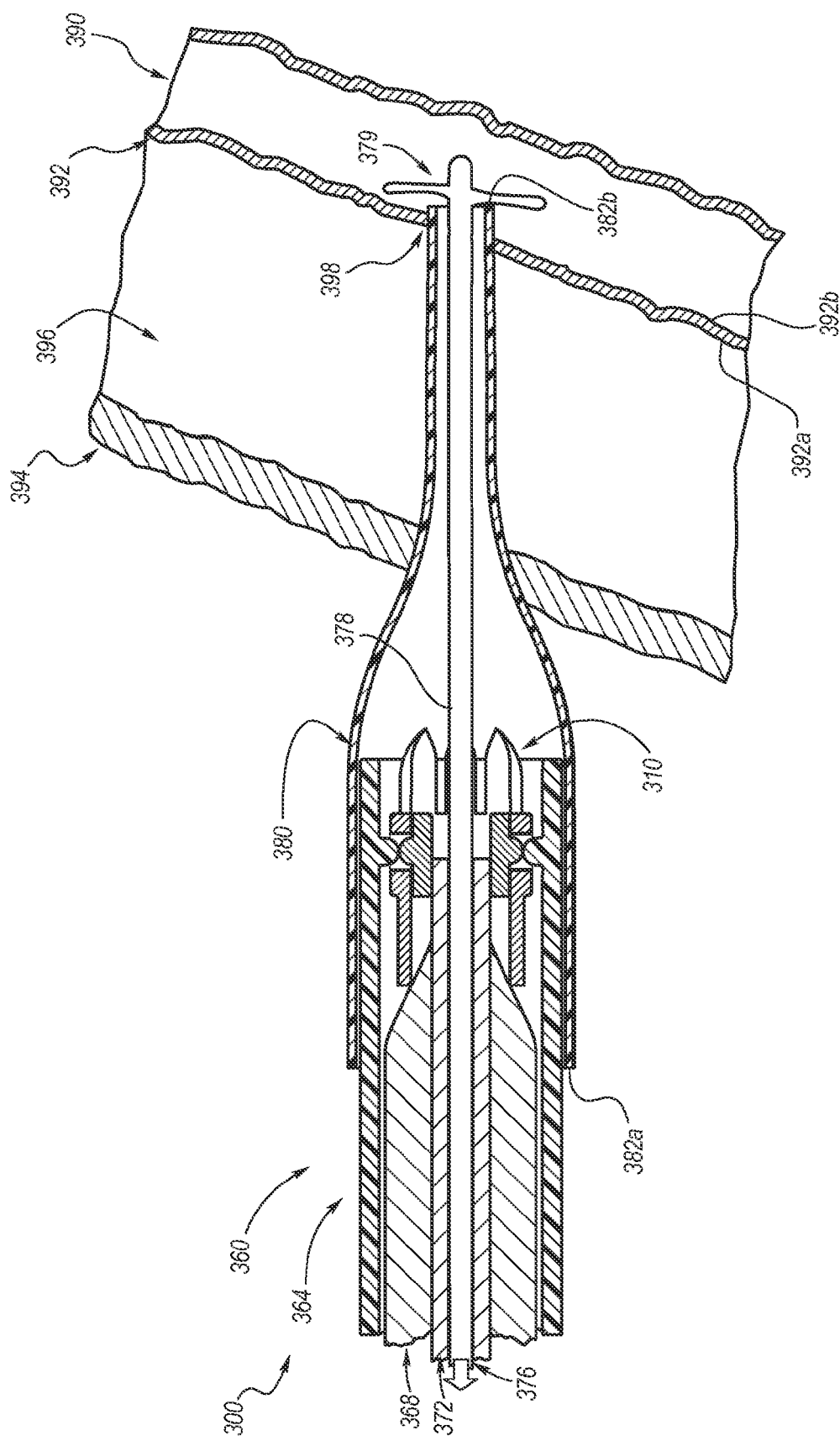

Once the distal end region 379 of the tubular body 378 extends into the blood vessel 390, the distal end region 379 may transition from the unexpanded state to the expanded state as shown in FIG. 3D. A triggering system (not shown) of the locator 376 may be used to transition from the unexpanded state to the expanded state. Locators other than the expandable locator may also be used. For instance, a bleedback lumen and/or other locator may be used to locate the body lumen. Alternatively, no locator may be used. Rather, the engaging element delivery device 360 may be advanced until a technician determines that the distal end is near the opening.

Figure 3E:
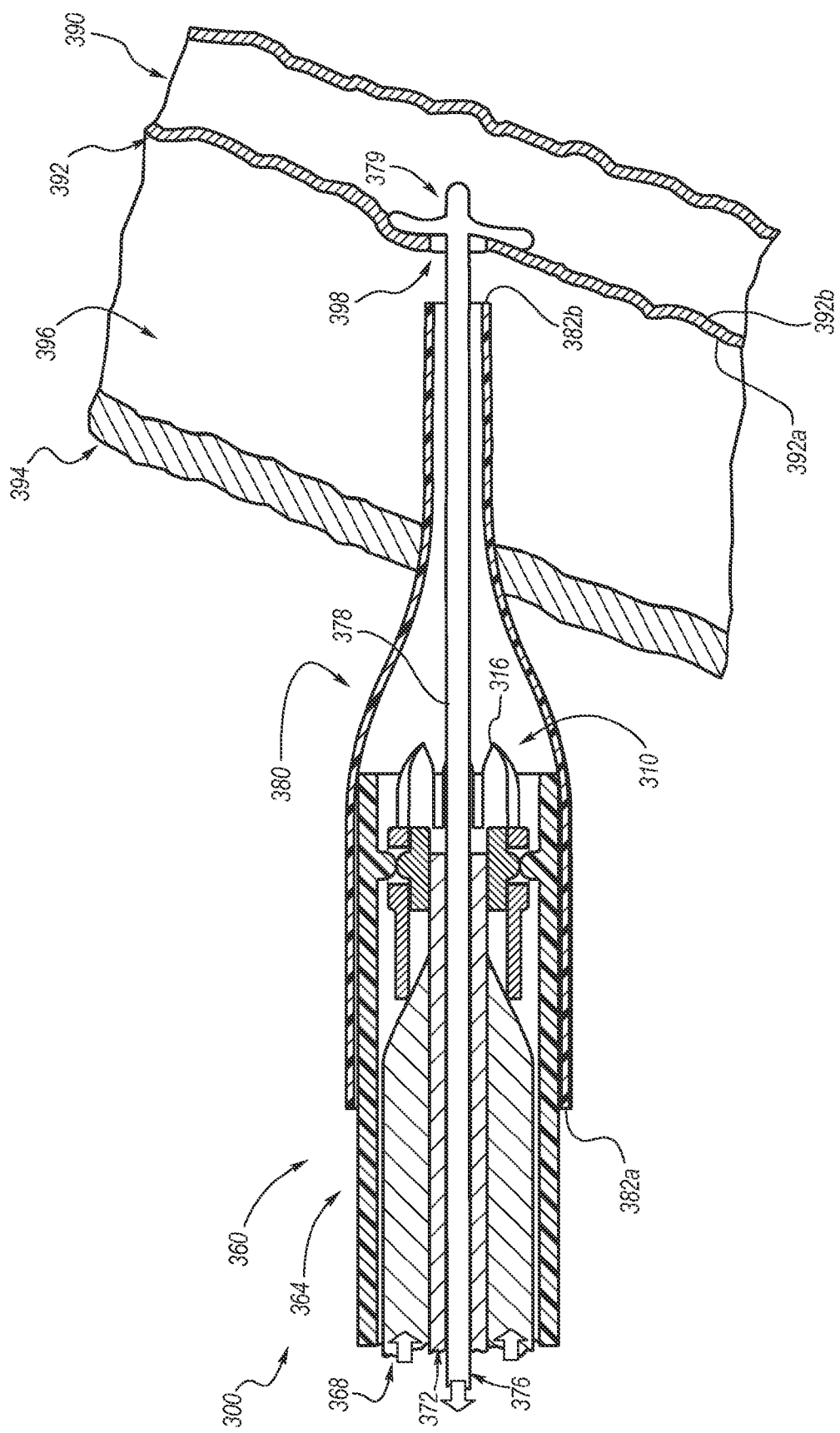

Turning to FIG. 3E, the engaging element delivery device 360 and the sheath 380 may be retracted proximally until the distal end region 379 is substantially adjacent to an inner surface 392b of the blood vessel wall 392. The distal end region 379 thereby may draw the blood vessel wall 392 taut and/or may maintain the proper position of the system 300 as the blood vessel 390 pulsates. Since the expanded cross-section of the distal end region 379 can be greater than or substantially equal to the cross-section of the opening 398 and/or the cross-section of the lumen 384, the distal end region 379 may remain in the blood vessel 390 and may engage the inner surface 392b of the blood vessel wall 392. The distal end region 379 may frictionally engage the inner surface 392b of the blood vessel wall 392, thereby securing the system 300 to the blood vessel 390. The sheath 380 can be retracted proximally such that the distal end region 382b of the sheath 380 may be substantially withdrawn from the blood vessel 390, as shown in FIG. 3E, permitting system 300 to access the blood vessel wall 392.

Figure 3F:
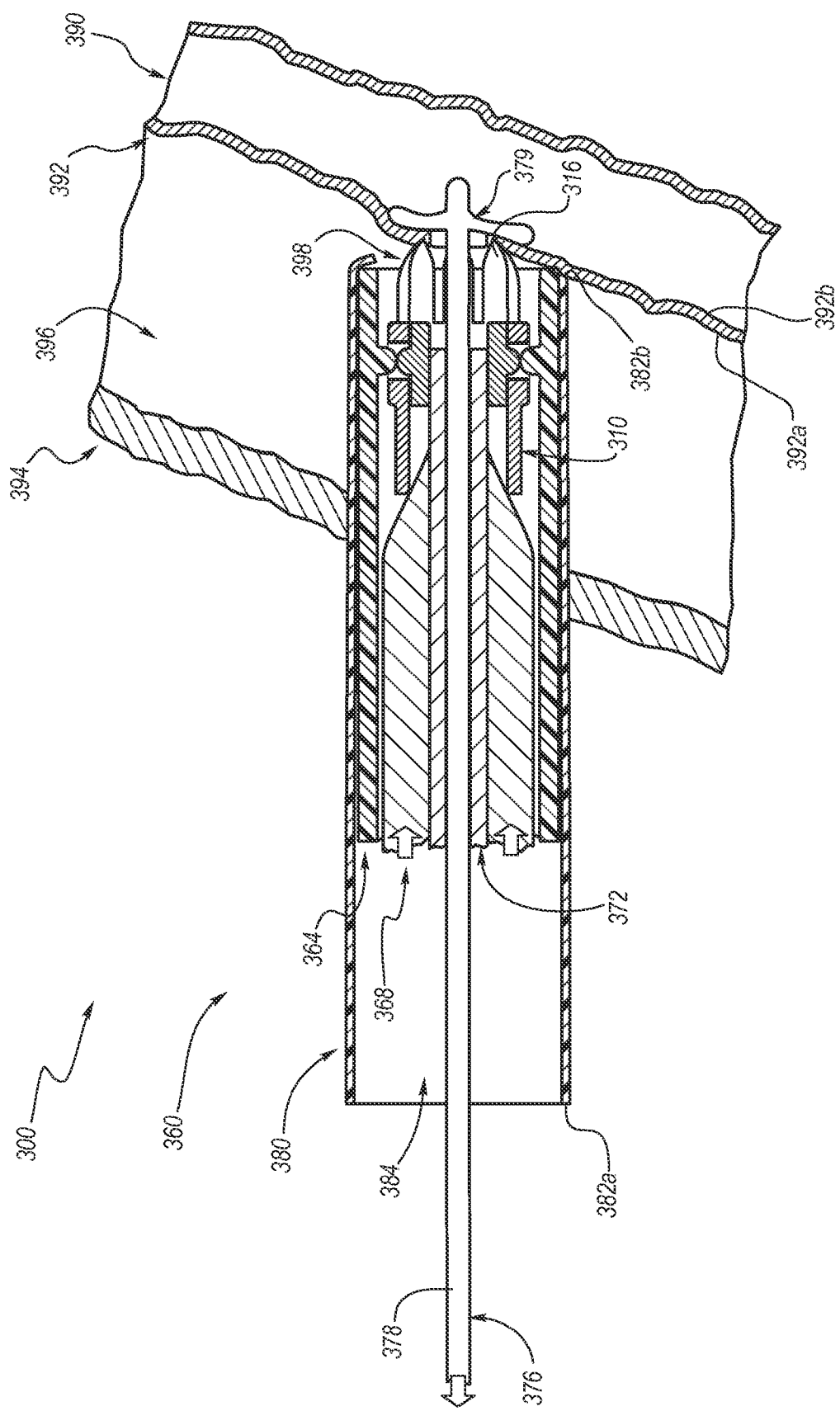

Once the distal end region 379 of the locator 376 contacts the inner surface 392b of the blood vessel wall 392, the engaging element delivery device 360 may be advanced distally and may be received within the lumen 384 of the sheath 380 as illustrated in FIG. 3F. The sheath 380 may radially expand and/or split in accordance with the predetermined pattern as the distal portion advances because the internal cross-section of the sheath 380 may be less than an outer portion of the retaining member 364.

Upon reaching the first predetermined position, the distal portion of the retaining member 364 can be disposed substantially adjacent to the outer surface 392a of the blood vessel wall 392 adjacent to the opening 398 such that the blood vessel wall 392 adjacent to the opening 398 may be disposed substantially between the expanded distal region 379 of the locator 376 and the distal portion of the retaining member 364. The engaging element 310 and retaining member 364 may be configured such that as the retaining member 364 approaches the distal end 379 of the locator 376, the tissue engaging portions 316 of the engaging member 310 may engage the outer portion 392a of the vessel wall 392.

Figure 3G:
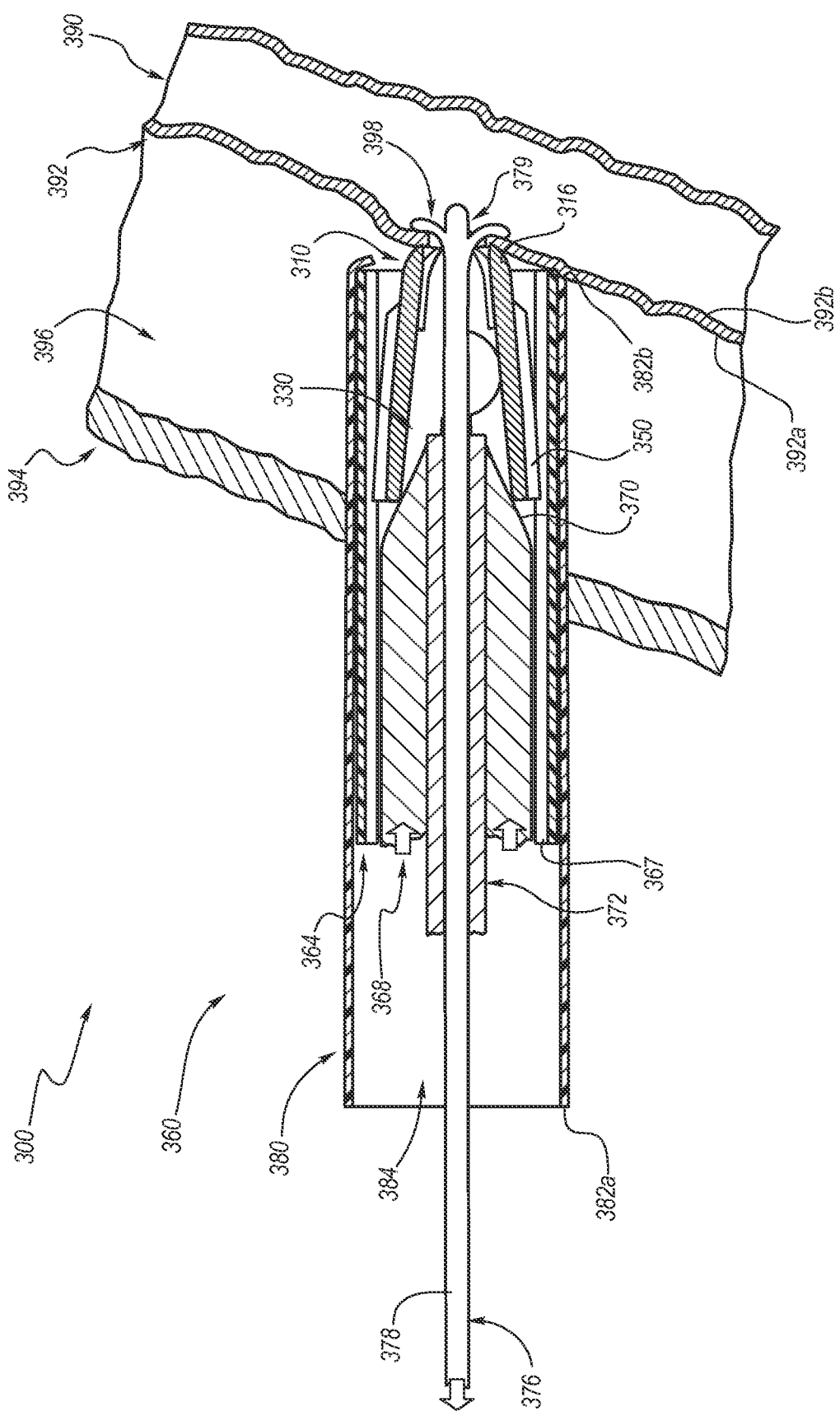
Figure 3H:
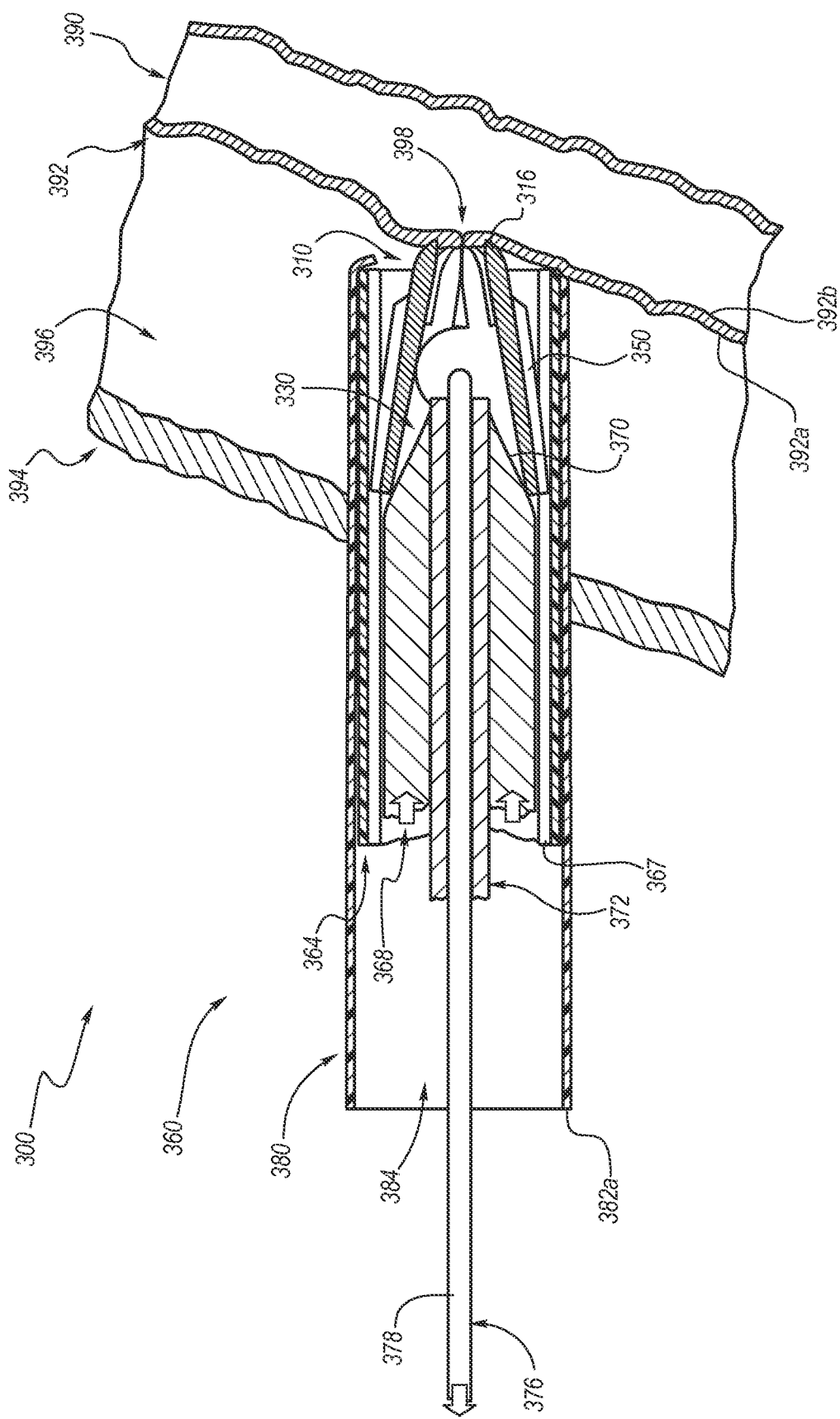

As shown in FIG. 3G, which is rotated ninety degrees to illustrate the interaction of the first member 312 and second member 314 of the engaging element 310 during deployment, the transitioning member 368 may advance distally to cause the tissue engaging portions 316 of the engaging member 310 to move toward the closed configuration (i.e. from the first distal dimension to the second distal dimension). The convex transitioning surface 370 may cause the transitioning portion 330 of the engaging element 310 to transition toward the closed configuration (i.e. the proximal ends of the first member 312 and the second member 314 may move away from each other while the tissue engaging portions 316 move toward each other).

Alternatively, other transitioning members 368 and/or engaging elements 310 may be used. For example, the transitioning member 268 and engaging element 210 described in connection with FIGS. 2A-2D may be used, such that the concave transitioning surface 270 may cause the transitioning portion 230 of the engaging element 210 to transition toward the closed configuration (i.e. the proximal ends of the first member 212 and the second member 214 may move toward each other).

As the tissue engaging portions 316 move toward each other, the distal end 379 of the locator 376 may move toward the unexpanded configuration and/or begin to move proximally to allow the tissue engaging portions 316 to fully engage the vessel wall 392. Alternatively, the locator 376 may remain within the blood vessel 390 after the tissue engaging portions 316 have engaged the vessel wall 392 and/or may be later removed.

Figure 3I:
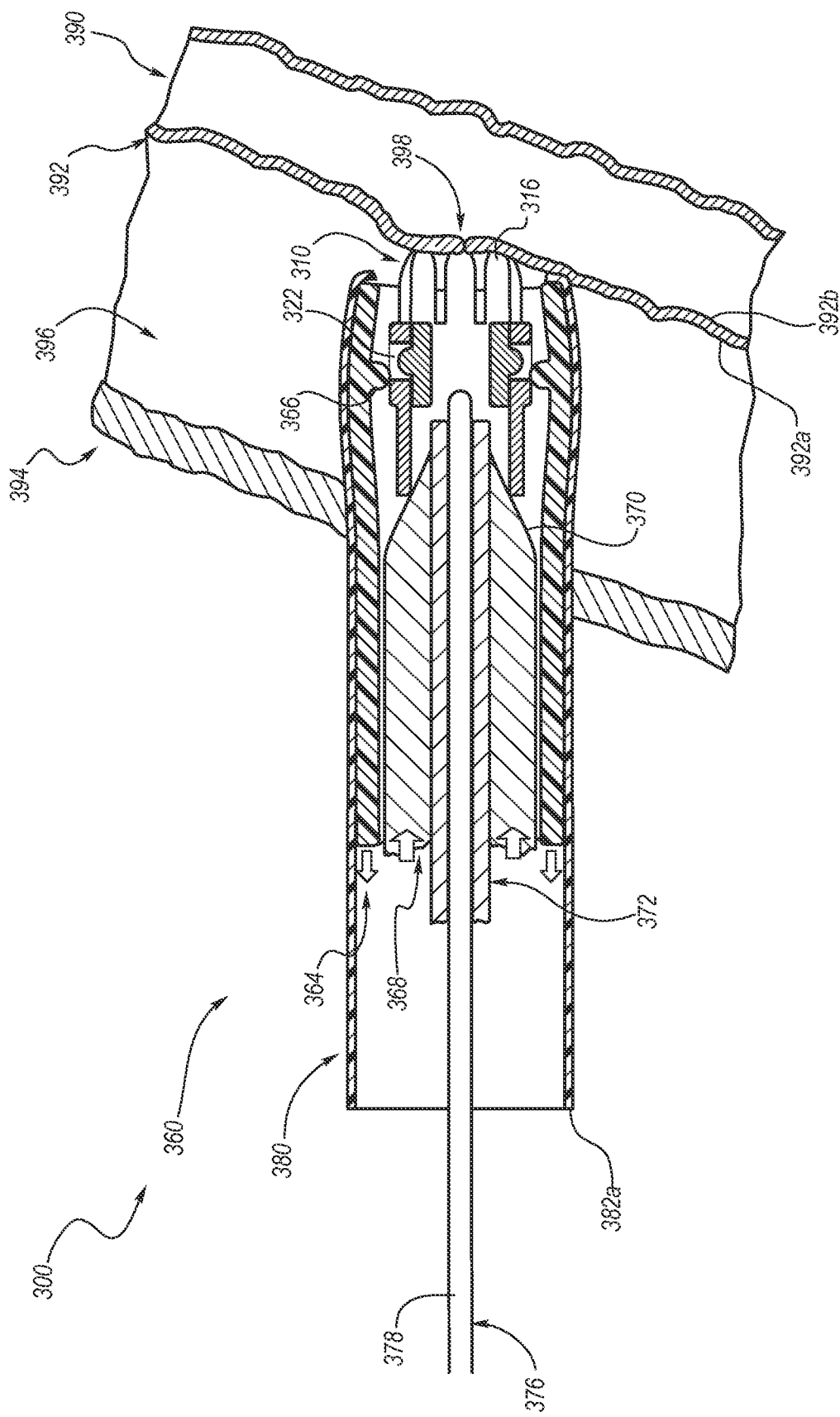
Figure 3J:
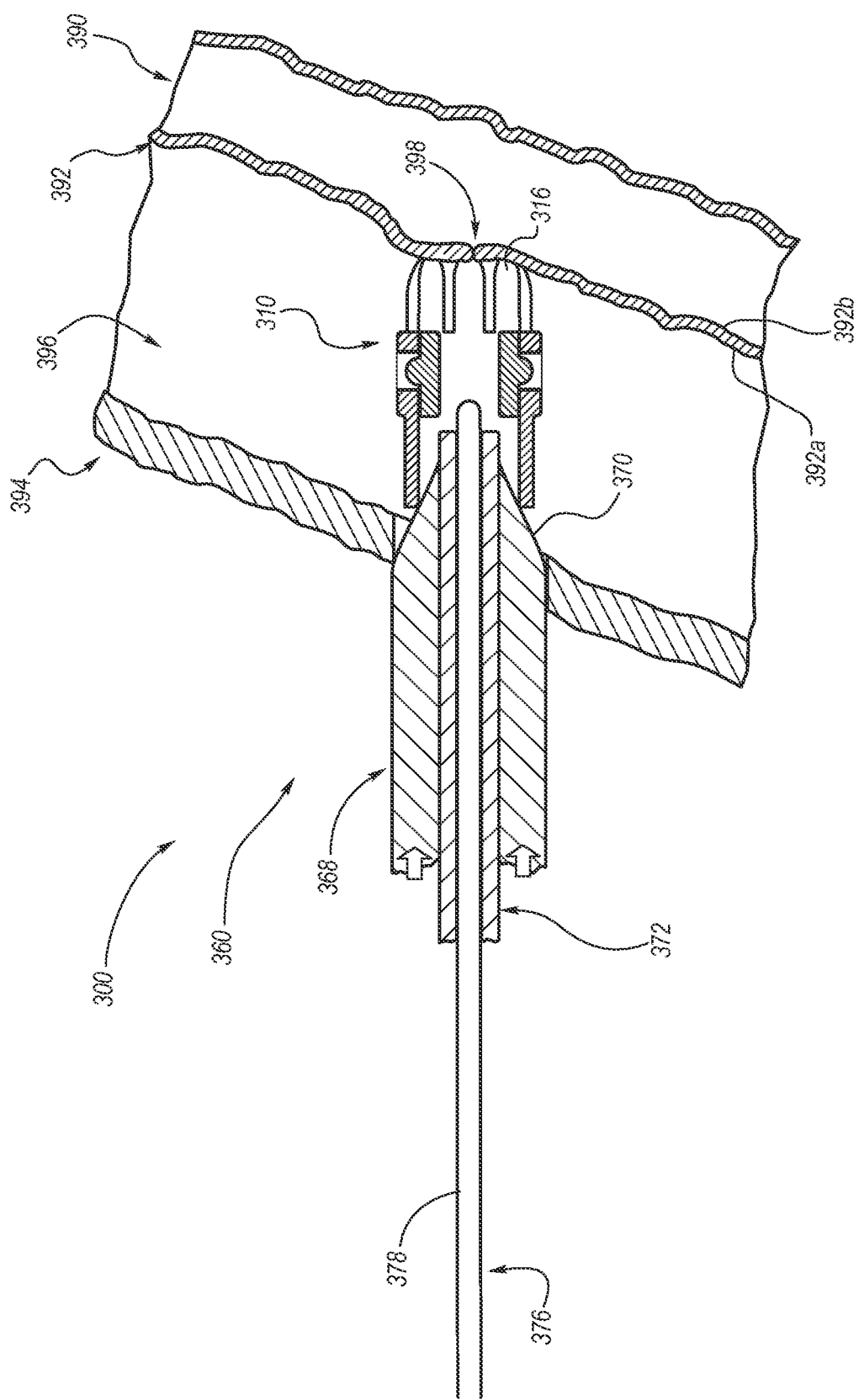

As shown in FIGS. 3H-3L, the engaging element 310 may be deployed. The engaging element 310 may engage the vessel wall 392 (as shown in FIG. 3F) in the open configuration. For instance, the tissue engaging portions 316 may frictionally, piercingly, and/or otherwise engage the vessel wall 392. As shown in FIG. 3I, the transitioning member 368 may continue to apply distal pressure to the engaging element 310 as the retaining member 364 begins to advance distally. The retaining member 364 may begin to disengage from the engaging element 310. For example, the retaining mechanism 366 may begin to be removed from the pivoting opening 322 of the engaging element 310, as shown in FIG. 3I. The retaining member 364 may be fully removed while the transitioning member 368 maintains distal pressure on the engaging element 310, as shown in FIG. 3J. Then the remaining components of the system 300 may be removed through the skin 394, as shown in FIG. 3K. The engaging element 310 may remain between the outer surface 392a of the vessel wall 392 and the skin 394, i.e. within the tissue 396, while in the closed configuration. The opening 398 in the skin 394 may be closed with a bandage or other device.

Access to the body lumen may be reestablished by unlocking the locking mechanism (140 shown in FIG. 1). For instance, a device (not shown) may be used to push the locking member and/or latch member out of engagement with the teeth and/or latching portion allowing the tissue engaging portions 316 to move away from each other toward the open configuration.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

I claim:

1. An engaging system for engaging tissue, the engaging system comprising:
    an engaging element for engaging tissue, said engaging element comprising:
        a first member including at least one tissue engaging portion having a sharpened tip, said sharpened tip extending distally from said first member;
        a second member including at least one tissue engaging portion and being pivotally connected to said first member;
        an elongate aligning portion located on at least one of the first member and the second member, the elongate aligning portion extending along a length and transversely from a surface of at least one of the first member and the second member;
    a pivoting mechanism operatively associated with said first and said second member wherein said pivoting mechanism comprises a pivoting opening located on one of said first member and said second member and a pivoting member located on the other of said first member and said second member, and said pivoting member engaging the pivoting opening;
    a locking mechanism operatively associated with said first member and said second member, said locking mechanism being configured to inhibit relative motion between said first member and said second member; and
    a retaining member, said retaining member comprising a retaining mechanism configured to limit motion of the engaging element both longitudinally through the retaining member and radially about an axis within the retaining member, said retaining member further comprising an aligning mechanism which is operatively associated with said elongate aligning portion, said aligning mechanism being complementary to said elongate aligning portion to receive said elongate aligning portion; and
    an engaging element delivery device, said engaging element delivery device comprising a transitioning member, said transitioning member being configured to transition said engaging element from an open configuration toward a closed configuration,
    wherein said retaining mechanism is engaged with said pivoting opening to selectably inhibit relative motion between said engaging element and said retaining member.

2. The engaging system of claim 1, wherein said first member and said second member further comprise a proximal end, said proximal end of said first member and said proximal end of said second member being separated by a first transitioning dimension in said open configuration and being separated by a second transitioning dimension in said closed configuration.

3. The engaging system of claim 2, wherein said first transitioning dimension is larger than said second transitioning dimension.

4. The engaging system of claim 2, wherein said first transitioning dimension is smaller than said second transitioning dimension.

5. The engaging system of claim 1, wherein said locking mechanism comprises a first locking portion and a second locking portion, relative movement of said at least one tissue engaging portion of said first member and said at least one tissue engaging portion of said second member being inhibited by operative association between said first locking portion and said second locking portion.

6. The engaging system of claim 5, wherein said first locking portion comprises at least one tooth located on said first member and said second locking portion comprising a locking member located on said second member.

7. The engaging system of claim 6, wherein said locking member and said at least one tooth inhibit said at least one tissue engaging portion of said first member and said at least one tissue engaging portion of said second member from opening.

8. The engaging system of claim 6, wherein said locking member is biased toward said at least one tooth.

9. The engaging system of claim 5, wherein said first locking portion comprises a latch located on said first member and said second locking portion comprising a latching portion located on said second member.

10. The engaging system of claim 9, wherein said latch and said latching portion inhibit said at least one tissue engaging portion of said first member and said at least one tissue engaging portion of said second member from opening.

11. The engaging system of claim 1, wherein said at least one tissue engaging portion of said first member and said at least one tissue engaging portion of said second member are separated by a first distal dimension in said open configuration and are separated by a second distal dimension in said closed configuration, said first distal dimension being larger than said second distal dimension.

12. The engaging system of claim 1, wherein said engaging element comprises bioabsorbable, biodegradable, and/or bioerodible material.

13. The engaging system of claim 12, wherein said engaging element further comprises collagen, polycaprolactone (PCL), poly-D,L-lactic acid, Poly-L-lactic acid, poly (lactide-co-glycolide), poly(hydroxybutyrate), polyanhydrides, and/or poly(glycolic acid).

14. The engaging system of claim 1, wherein said retaining mechanism further comprises a retaining detent that engages said pivoting opening to selectably inhibit the relative motion between said engaging element and said retaining member.

15. The engaging system of claim 1, wherein said retaining member and said transitioning member are axially aligned.

16. The engaging system of claim 1, wherein said retaining member is configured to slidably receive said transitioning member.

17. The engaging system of claim 1, wherein said first member and said second member of said engaging element further comprise a transitioning portion, said transitioning member comprising a transitioning surface, said transitioning surface being shaped to engage with said transitioning portion of at least one of said first member and said second member of said engaging element.

18. The engaging system of claim 17, wherein said transitioning surface has a convex shape.

19. The engaging system of claim 17, wherein said transitioning surface has a concave shape.

* * * * *